US009597237B2

(12) United States Patent
Enz et al.

(10) Patent No.: US 9,597,237 B2
(45) Date of Patent: Mar. 21, 2017

(54) ABSORBENT ARTICLE HAVING A FASTENING SYSTEM

(71) Applicant: Kimberly-Clark Worldwide, Inc., Neenah, WI (US)

(72) Inventors: David John Enz, Neenah, WI (US); Sara Jane Wille Stabelfeldt, Appleton, WI (US); Robert Lee Popp, Greenville, WI (US); David Fleger Bishop, Appleton, WI (US); Wendy Lynn Vandyke, Appleton, WI (US)

(73) Assignee: Kimberly-Clark Worldwide, Inc, Neenah, WI (US)

( * ) Notice: Subject to any disclaimer, the term of this patent is extended or adjusted under 35 U.S.C. 154(b) by 510 days.

(21) Appl. No.: 14/144,833

(22) Filed: Dec. 31, 2013

(65) Prior Publication Data
US 2015/0182390 A1 Jul. 2, 2015

(51) Int. Cl.
*A61F 13/15* (2006.01)
*A61F 13/56* (2006.01)
(Continued)

(52) U.S. Cl.
CPC ........ *A61F 13/5644* (2013.01); *A61F 13/622* (2013.01); *A61F 13/5633* (2013.01);
(Continued)

(58) Field of Classification Search
CPC ...... A61F 13/62; A61F 13/622; A61F 13/625; A61F 13/627; A61F 13/581;
(Continued)

(56) References Cited

U.S. PATENT DOCUMENTS 3,848,594 A    11/1974   Buell
4,010,754 A    3/1977   Pieniak
(Continued)

FOREIGN PATENT DOCUMENTS

EP    0 217 032 A2    4/1987
EP    0 233 704 B1    7/1992
(Continued)

OTHER PUBLICATIONS

Co-pending U.S. Appl. No. 13/953,364, filed Jul. 29, 2013, by Popp et al. for "Tailored Peel for Secondary Fastener to Optimize Ease of Opening Product."
(Continued)

*Primary Examiner* — Jacqueline Stephens
(74) *Attorney, Agent, or Firm* — Kimberly-Clark Worldwide, Inc.

(57) ABSTRACT

An absorbent article is provided. The absorbent article includes an absorbent assembly having a liquid permeable inner layer, an outer layer, and an absorbent body between the inner and outer layers. A pair of ears extend transversely outward from opposite sides of the absorbent assembly in a back waist region, each of the ears having a primary first fastening-component that is selectively engagable with a primary second fastening-component in a front waist region. There is a pair of spaced-apart secondary first fastening-components disposed on the outer layer in the front waist region, each of the secondary first fastening-components being selectively engageable with the secondary second fastening-components. Each secondary first fastening-component fits into a fastener region, wherein each fastener region is defined by an outline. Each outline has a waist edge and an opposite leg edge connected by an outer edge and an inner edge. The length of the outer edge is shorter than the length of the inner edge.

20 Claims, 23 Drawing Sheets

(51) Int. Cl.
*A61F 13/62* (2006.01)
*A61F 13/58* (2006.01)

(52) U.S. Cl.
CPC .......... *A61F 13/581* (2013.01); *A61F 13/625* (2013.01); *A61F 13/627* (2013.01); *A61F 2013/5666* (2013.01); *A61F 2013/583* (2013.01); *A61F 2013/585* (2013.01); *A61F 2013/587* (2013.01); *A61F 2013/588* (2013.01)

(58) Field of Classification Search
CPC .............. A61F 13/5644; A61F 13/5633; A61F 2013/583; A61F 2013/585; A61F 2013/587; A61F 2013/588; A61F 2013/566; A61F 2013/5666; A61F 2013/5677
USPC ................................ 604/391, 394, 396, 389
See application file for complete search history.

(56) References Cited

U.S. PATENT DOCUMENTS

| | | |
|---|---|---|
| 4,041,203 A | 8/1977 | Brock et al. |
| 4,050,462 A | 9/1977 | Woon et al. |
| 4,253,461 A | 3/1981 | Strickland et al. |
| 4,374,888 A | 2/1983 | Bornslaeger |
| 4,402,690 A | 9/1983 | Redfern |
| 4,500,316 A | 2/1985 | Damico |
| 4,581,772 A | 4/1986 | Smith |
| 4,585,448 A | 4/1986 | Enloe |
| 4,662,875 A | 5/1987 | Hirotsu et al. |
| 4,663,220 A | 5/1987 | Wisneski et al. |
| 4,699,622 A | 10/1987 | Toussant et al. |
| 4,701,179 A | 10/1987 | Kellenberger et al. |
| 4,753,650 A | 6/1988 | Williams |
| 4,766,029 A | 8/1988 | Brock et al. |
| 4,770,656 A | 9/1988 | Proxmire et al. |
| 4,773,906 A | 9/1988 | Krushel |
| 4,801,298 A | 1/1989 | Sorenson et al. |
| 4,846,815 A | 7/1989 | Scripps |
| 4,850,988 A | 7/1989 | Aledo et al. |
| 4,850,992 A | 7/1989 | Amaral et al. |
| 4,869,724 A | 9/1989 | Scripps |
| 4,894,060 A | 1/1990 | Nestegard |
| 4,923,456 A | 5/1990 | Proxmire |
| 4,936,840 A | 6/1990 | Proxmire |
| 4,938,753 A | 7/1990 | Van Gompel et al. |
| 4,940,464 A | 7/1990 | Van Gompel et al. |
| 4,946,527 A | 8/1990 | Battrell |
| 4,988,346 A | 1/1991 | Pfefferkorn |
| 5,019,072 A | 5/1991 | Polski |
| 5,019,073 A | 5/1991 | Roessler et al. |
| 5,046,272 A | 9/1991 | Vogt et al. |
| 5,069,678 A | 12/1991 | Yamamoto et al. |
| 5,104,116 A | 4/1992 | Pohjola |
| 5,108,384 A | 4/1992 | Goulait |
| 5,151,092 A | 9/1992 | Buelle et al. |
| 5,169,706 A | 12/1992 | Collier, IV et al. |
| 5,176,670 A | 1/1993 | Roessler et al. |
| 5,176,671 A | 1/1993 | Roessler et al. |
| 5,213,881 A | 5/1993 | Timmons et al. |
| 5,224,405 A | 7/1993 | Pohjola |
| 5,226,992 A | 7/1993 | Morman |
| 5,231,738 A | 8/1993 | Higashinaka |
| 5,242,436 A | 9/1993 | Weil et al. |
| 5,260,015 A | 11/1993 | Kennedy et al. |
| 5,279,604 A | 1/1994 | Robertson et al. |
| 5,325,569 A | 7/1994 | Goulait et al. |
| 5,358,500 A | 10/1994 | Lavon et al. |
| 5,368,585 A | 11/1994 | Dokken |
| 5,370,634 A | 12/1994 | Ando et al. |
| 5,383,871 A | 1/1995 | Carlin et al. |
| 5,392,498 A | 2/1995 | Gouliait et al. |
| 5,399,219 A | 3/1995 | Roessler et al. |
| 5,403,302 A | 4/1995 | Roessler et al. |
| 5,409,476 A | 4/1995 | Coates |
| 5,423,789 A | 6/1995 | Kuen |
| 5,464,688 A | 11/1995 | Timmons et al. |
| 5,518,795 A | 5/1996 | Kennedy et al. |
| 5,531,732 A | 7/1996 | Wood |
| 5,554,143 A | 9/1996 | Roe et al. |
| 5,593,401 A | 1/1997 | Sosalla et al. |
| 5,599,338 A | 2/1997 | Enloe |
| 5,603,794 A | 2/1997 | Thomas et al. |
| 5,605,735 A | 2/1997 | Zehner et al. |
| 5,611,789 A | 3/1997 | Seth |
| 5,624,428 A | 4/1997 | Sauer |
| 5,624,429 A | 4/1997 | Long et al. |
| 5,643,651 A | 7/1997 | Murasaki |
| H001674 H | 8/1997 | Ames et al. |
| 5,669,120 A | 9/1997 | Wessels et al. |
| 5,674,215 A | 10/1997 | Roennberg |
| 5,685,873 A | 11/1997 | Bruemmer |
| 5,744,080 A | 4/1998 | Kennedy et al. |
| 5,759,317 A | 6/1998 | Justmann |
| 5,766,389 A | 6/1998 | Brandon et al. |
| 5,766,723 A | 6/1998 | Oborny et al. |
| 5,782,819 A | 7/1998 | Tanzer et al. |
| 5,797,896 A | 8/1998 | Schmitz |
| 5,830,206 A | 11/1998 | Larsson |
| 5,846,262 A | 12/1998 | Sayama et al. |
| 5,851,467 A | 12/1998 | Murasaki |
| 5,858,515 A | 1/1999 | Stokes et al. |
| 5,984,911 A | 11/1999 | Siebers et al. |
| 5,997,522 A | 12/1999 | Provost et al. |
| 6,030,373 A | 2/2000 | VanGompel et al. |
| 6,045,543 A | 4/2000 | Pozniak et al. |
| 6,056,732 A | 5/2000 | Fujioka et al. |
| 6,063,066 A | 5/2000 | Inoue et al. |
| 6,099,516 A | 8/2000 | Pozniak et al. |
| 6,102,901 A | 8/2000 | Lord et al. |
| 6,142,983 A | 11/2000 | Suprise et al. |
| 6,142,986 A | 11/2000 | Lord et al. |
| 6,174,303 B1 | 1/2001 | Surprise et al. |
| 6,174,476 B1 | 1/2001 | Kennedy et al. |
| 6,248,419 B1 | 6/2001 | Kennedy et al. |
| 6,264,644 B1 | 7/2001 | Igaue et al. |
| 6,287,287 B1 | 9/2001 | Elsberg |
| 6,302,871 B1 | 10/2001 | Nakao et al. |
| 6,322,552 B1 | 11/2001 | Blenke et al. |
| 6,371,949 B1 | 4/2002 | Soga et al. |
| 6,371,951 B1 | 4/2002 | Koczab et al. |
| 6,387,085 B1 | 5/2002 | Van Gompel et al. |
| 6,402,731 B1 | 6/2002 | Surprise et al. |
| 6,406,466 B1 | 6/2002 | Pozniak et al. |
| 6,454,752 B1 | 9/2002 | Huang et al. |
| 6,491,675 B1 | 12/2002 | Shimada et al. |
| 6,508,797 B1 | 1/2003 | Pozniak et al. |
| 6,524,293 B1 | 2/2003 | Elsberg et al. |
| 6,544,242 B1 | 4/2003 | Kido et al. |
| 6,551,294 B1 | 4/2003 | Elsberg et al. |
| 6,554,816 B1 | 4/2003 | Olson |
| 6,572,601 B2 | 6/2003 | Suprise et al. |
| 6,595,977 B1 | 7/2003 | Luizzi, Jr. et al. |
| 6,613,032 B2 | 9/2003 | Ronnberg et al. |
| 6,648,866 B2 | 11/2003 | Magee et al. |
| 6,682,512 B2 | 1/2004 | Uitenbroek et al. |
| 6,730,069 B2 | 5/2004 | Tanzer et al. |
| 6,733,483 B2 | 5/2004 | Raufman et al. |
| 6,736,804 B1 | 5/2004 | Robertson et al. |
| 6,737,147 B2 | 5/2004 | Kennedy et al. |
| 6,849,067 B2 | 2/2005 | Fletcher et al. |
| 6,890,630 B2 | 5/2005 | Franklin et al. |
| 6,893,426 B1 | 5/2005 | Popp et al. |
| 6,916,750 B2 | 7/2005 | Thomas et al. |
| 6,932,802 B2 | 8/2005 | Luizzi, Jr. et al. |
| 6,945,968 B2 | 9/2005 | Svensson et al. |
| 6,972,012 B1 | 12/2005 | Pozniak et al. |
| 6,976,978 B2 | 12/2005 | Ruman et al. |
| 6,994,697 B2 | 2/2006 | Shimada et al. |
| 6,994,698 B2 | 2/2006 | Leak et al. |
| 7,014,906 B2 | 3/2006 | Tuman et al. |
| 7,018,368 B2 | 3/2006 | Van Gompel et al. |
| 7,032,278 B2 | 4/2006 | Kurtz, Jr. |

(56) References Cited

U.S. PATENT DOCUMENTS

| | | |
|---|---|---|
| 7,122,024 B2 | 10/2006 | Nakajima et al. |
| 7,150,730 B2 | 12/2006 | Hasler et al. |
| 7,150,732 B2 | 12/2006 | Yoshida et al. |
| 7,150,733 B2 | 12/2006 | Yamakawa et al. |
| 7,156,833 B2 | 1/2007 | Couture-Dorscher et al. |
| 7,162,780 B2 | 1/2007 | Martin et al. |
| 7,175,584 B2 | 2/2007 | Maxton et al. |
| 7,189,220 B2 | 3/2007 | Miyoshi et al. |
| 7,198,621 B2 | 4/2007 | Moser et al. |
| 7,201,744 B2 | 4/2007 | Van Gompel et al. |
| 7,207,979 B2 | 4/2007 | Price et al. |
| 7,211,072 B2 | 5/2007 | Nawata et al. |
| 7,244,382 B2 | 7/2007 | Tachauer et al. |
| 7,252,658 B2 | 8/2007 | Sayama |
| 7,275,290 B2 | 10/2007 | Clarner et al. |
| 7,344,525 B2 | 3/2008 | Linker, III et al. |
| 7,422,783 B2 | 9/2008 | Tremblay et al. |
| 7,449,017 B2 | 11/2008 | Yoshida |
| 7,451,532 B2 | 11/2008 | Provost et al. |
| 7,455,665 B2 | 11/2008 | Wendelstorf et al. |
| 7,473,818 B2 | 1/2009 | Datta et al. |
| 7,534,481 B2 | 5/2009 | Seth et al. |
| 7,568,264 B2 | 8/2009 | Miyamoto et al. |
| 7,569,042 B2 | 8/2009 | Van Gompel et al. |
| 7,662,137 B2 | 2/2010 | Sayama et al. |
| 7,736,351 B2 | 6/2010 | Nigam et al. |
| 7,811,273 B2 | 10/2010 | Kline et al. |
| 7,828,784 B2 | 11/2010 | Popp et al. |
| 7,855,314 B2 | 12/2010 | Hanao et al. |
| 8,118,801 B2 | 2/2012 | Macura et al. |
| 8,211,077 B2 | 7/2012 | Sugiyama et al. |
| 8,353,891 B2 | 1/2013 | Hornung et al. |
| 8,395,017 B2 | 3/2013 | Nakahata et al. |
| 8,496,640 B2 | 7/2013 | Molander |
| 8,636,710 B2 | 1/2014 | Ellingson et al. |
| 2002/0016581 A1 | 2/2002 | Kline et al. |
| 2002/0032427 A1 | 3/2002 | Schmitz et al. |
| 2002/0095130 A1 | 7/2002 | Seitter et al. |
| 2002/0095132 A1 | 7/2002 | Ashton et al. |
| 2002/0107498 A1 | 8/2002 | Kling et al. |
| 2002/0123734 A1 | 9/2002 | Carlbark et al. |
| 2002/0138064 A1 | 9/2002 | Datta et al. |
| 2002/0165518 A1 | 11/2002 | Datta et al. |
| 2002/0169431 A1 | 11/2002 | Kline et al. |
| 2002/0173768 A1 | 11/2002 | Elsberg et al. |
| 2002/0174934 A1 | 11/2002 | Johnson et al. |
| 2003/0044578 A1 | 3/2003 | Nissing |
| 2003/0153891 A1 | 8/2003 | Molee |
| 2003/0233080 A1 | 12/2003 | Backman et al. |
| 2004/0122400 A1 | 6/2004 | Hancock et al. |
| 2004/0122413 A1 | 6/2004 | Roessler et al. |
| 2004/0129592 A1 | 7/2004 | Otsubo |
| 2004/0158224 A1 | 8/2004 | Kline et al. |
| 2004/0187275 A1 | 9/2004 | Kennedy et al. |
| 2004/0243091 A1 | 12/2004 | Mitsui et al. |
| 2004/0261233 A1 | 12/2004 | Kingsford et al. |
| 2005/0015069 A1 | 1/2005 | Hamilton et al. |
| 2005/0027271 A1 | 2/2005 | Popp et al. |
| 2005/0043700 A1 | 2/2005 | Otsubo et al. |
| 2005/0090793 A1 | 4/2005 | Winqvist |
| 2005/0143710 A1 | 6/2005 | Van Gompel et al. |
| 2005/0148976 A1 | 7/2005 | Van Gompel et al. |
| 2005/0148977 A1 | 7/2005 | Van Gompel et al. |
| 2005/0148982 A1 | 7/2005 | Van Gompel et al. |
| 2005/0148985 A1 | 7/2005 | Bronk et al. |
| 2005/0148986 A1 | 7/2005 | Collins et al. |
| 2005/0217791 A1 | 10/2005 | Costello et al. |
| 2005/0222551 A1 | 10/2005 | Otsubo |
| 2006/0004337 A1 | 1/2006 | Datta |
| 2006/0069376 A1 | 3/2006 | Miller |
| 2006/0069378 A1 | 3/2006 | Winkel et al. |
| 2006/0241561 A1 | 10/2006 | De Angelis |
| 2006/0247594 A1 | 11/2006 | Nickel et al. |
| 2006/0247597 A1 | 11/2006 | Hogan et al. |
| 2006/0264861 A1 | 11/2006 | Lavon et al. |
| 2006/0266465 A1 | 11/2006 | Meyer |
| 2006/0293639 A1 | 12/2006 | Van Gompel et al. |
| 2007/0032773 A1 | 2/2007 | Magee et al. |
| 2007/0083177 A1 | 4/2007 | Takino et al. |
| 2007/0093769 A1 | 4/2007 | Kline et al. |
| 2007/0112321 A1 | 5/2007 | Goates et al. |
| 2007/0157441 A1 | 7/2007 | Kline et al. |
| 2007/0250026 A1 | 10/2007 | Venturino et al. |
| 2008/0058753 A1 | 3/2008 | Dalal |
| 2008/0086104 A1 | 4/2008 | Karlsson |
| 2008/0091163 A1 | 4/2008 | Fujioka |
| 2008/0097363 A1 | 4/2008 | Fernfors et al. |
| 2008/0114323 A1 | 5/2008 | Kline et al. |
| 2008/0132863 A1 | 6/2008 | Waksmundzki et al. |
| 2008/0154227 A1 | 6/2008 | Andersson et al. |
| 2008/0172840 A1 | 7/2008 | Kacker et al. |
| 2008/0312624 A1 | 12/2008 | Hundorf et al. |
| 2009/0076783 A1 | 3/2009 | Babusik et al. |
| 2009/0198207 A1 | 8/2009 | Torigoshi et al. |
| 2009/0299317 A1 | 12/2009 | Flannery |
| 2009/0299318 A1 | 12/2009 | Faulks et al. |
| 2009/0299322 A1 | 12/2009 | Faulks et al. |
| 2009/0299323 A1 | 12/2009 | Schlinz et al. |
| 2010/0234822 A1 | 9/2010 | Baeck |
| 2010/0241096 A1 | 9/2010 | Lavon et al. |
| 2011/0100526 A1 | 5/2011 | Umebayashi |
| 2011/0168318 A1 | 7/2011 | Nilsson et al. |
| 2012/0157958 A1 | 6/2012 | Tenorio et al. |
| 2012/0245548 A1 | 9/2012 | Matsushima et al. |
| 2013/0067701 A1 | 3/2013 | Grady et al. |
| 2013/0211361 A1 | 8/2013 | Anderson et al. |
| 2013/0310794 A1 | 11/2013 | Faulks et al. |
| 2014/0046284 A1 | 2/2014 | Dougherty, Jr. et al. |
| 2014/0046287 A1 | 2/2014 | Martin et al. |
| 2014/0350507 A1 | 11/2014 | Pariseau et al. |
| 2015/0025491 A1 | 1/2015 | Sakaguchi et al. |

FOREIGN PATENT DOCUMENTS

| | | |
|---|---|---|
| EP | 0 476 992 B1 | 7/1995 |
| EP | 1 600 132 A1 | 11/2005 |
| EP | 1 299 063 B1 | 3/2006 |
| EP | 1 688 117 A1 | 8/2006 |
| EP | 2 335 504 B1 | 4/2013 |
| GB | 2 033 210 A | 5/1980 |
| JP | 01-062303 U1 | 4/1989 |
| JP | 01-092403 A | 4/1989 |
| JP | 02-088626 U1 | 7/1990 |
| JP | 07-227403 A | 8/1995 |
| JP | 08-005691 Y2 | 2/1996 |
| JP | 08-252281 A | 10/1996 |
| JP | 2003-079666 A | 3/2003 |
| JP | 2006-280664 A | 10/2006 |
| JP | 2007-209457 A | 8/2007 |
| JP | 2008-079867 A | 4/2008 |
| WO | WO 97/46197 A1 | 12/1997 |
| WO | WO 98/35642 A1 | 8/1998 |
| WO | WO 00/27328 A1 | 5/2000 |
| WO | WO 00/35397 A1 | 6/2000 |
| WO | WO 01/88245 A2 | 11/2001 |
| WO | WO 2013/097878 A1 | 7/2013 |
| WO | WO 2013/115347 A1 | 8/2013 |

OTHER PUBLICATIONS

Co-pending U.S. Appl. No. 13/953,396, filed Jul. 29, 2013, by Hancock-Cooke et al. for "Lower Bending Stiffness of Secondary Fastener to Enhance Skin Comfort."

Co-pending U.S. Appl. No. 13/953,380, filed Jul. 29, 2013, by Stabelfeldt et al. for "Absorbent Article Having a Fastening System."

Co-pending U.S. Appl. No. 14/070,996, filed Nov. 4, 2013, by Hancock-Cooke et al. for "Improved Leg Fit Through Addition of Anchor Points to the Stretch Ear."

Co-pending U.S. Appl. No. 14/071,262, filed Nov. 4, 2013, by Stabelfeldt et al. for "Absorbent Article Having a Fastening System Adapted to Enhance Gasketing."

(56) References Cited

OTHER PUBLICATIONS

Co-pending U.S. Appl. No. 14/091,838, filed Nov. 27, 2013, by Collins et al. for "A Secondary Hook Feature With a Contrasting Color Appearance From the Surrounding Graphic Print."

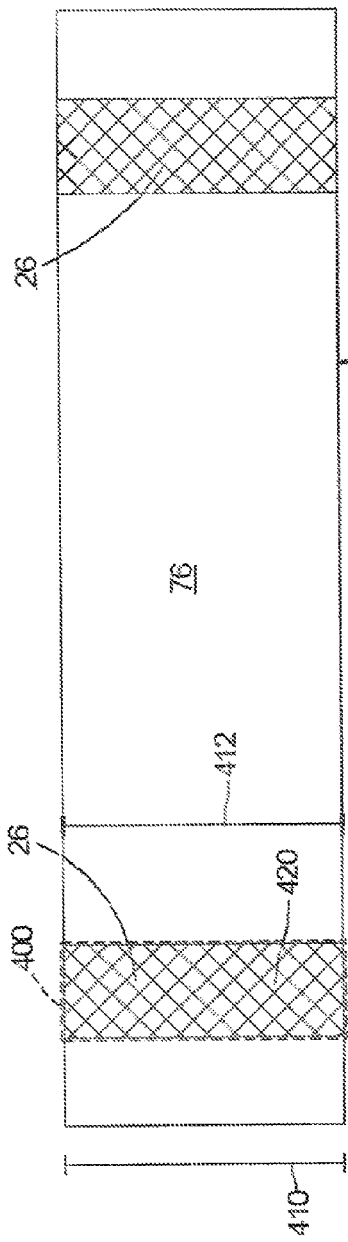
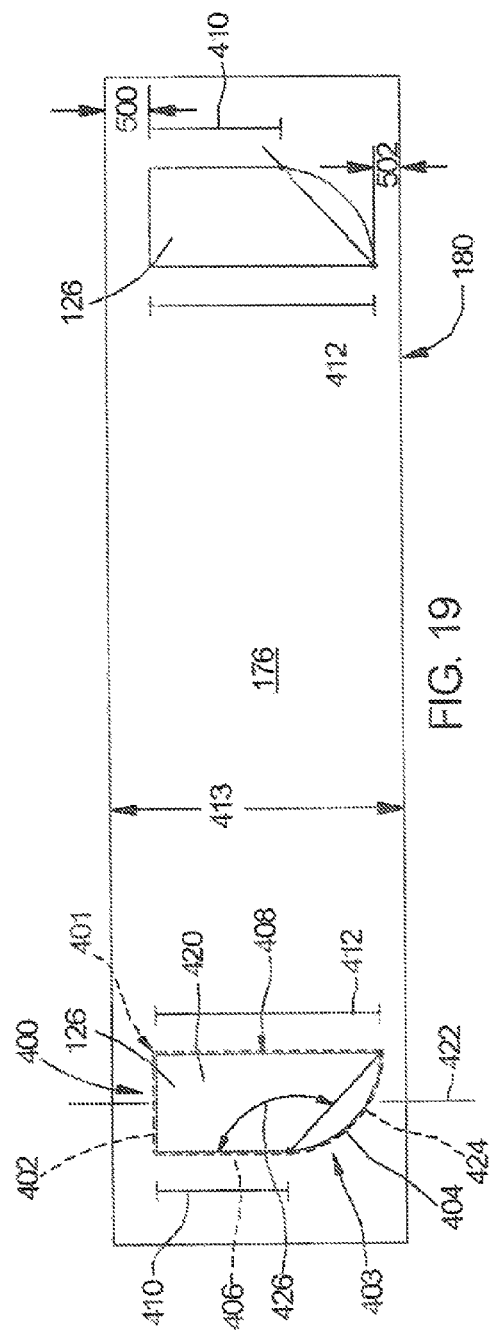

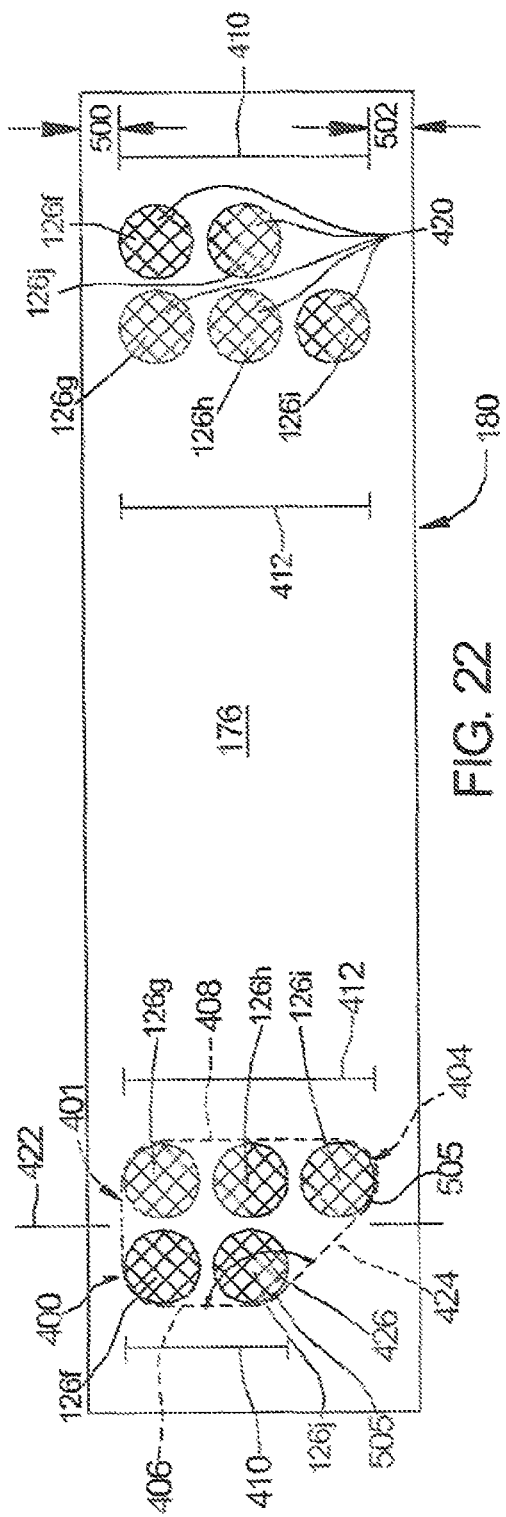
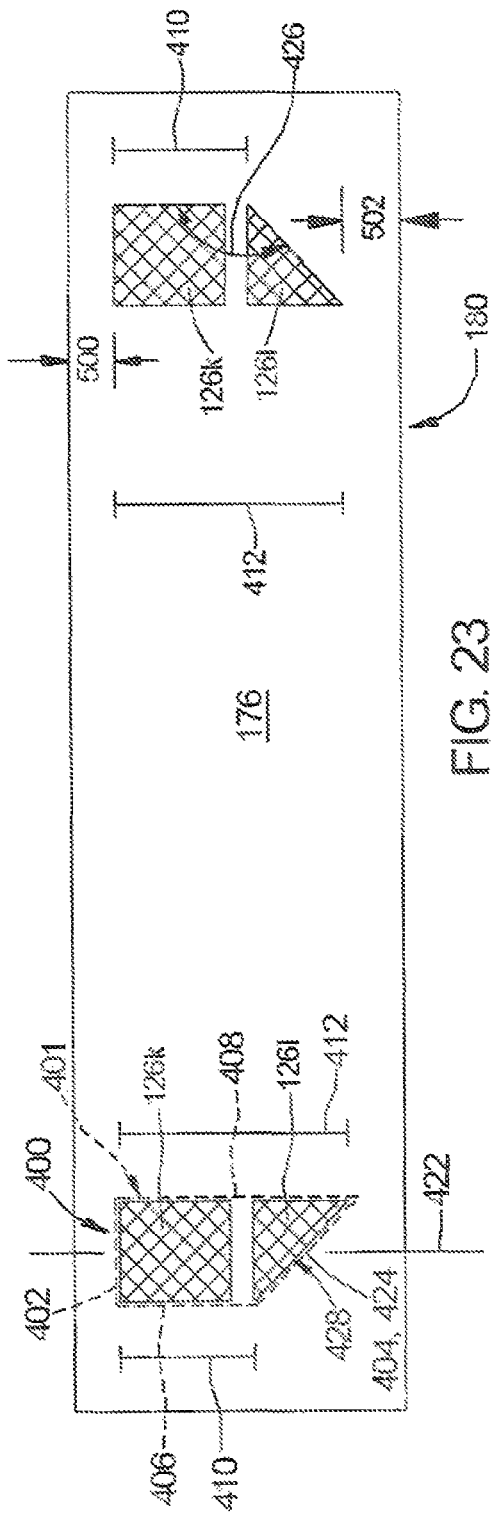
FIG. 22
FIG. 23

ABSORBENT ARTICLE HAVING A FASTENING SYSTEM

BACKGROUND

The present disclosure relates generally to absorbent articles intended for personal wear, and more particularly to disposable absorbent articles having a fastening system for selectively fastening and refastening the article about the wearer.

Many absorbent articles intended for personal wear, such as diapers, training pants, feminine hygiene products, adult incontinence products, bandages, medical garments and the like are designed to be sufficiently absorbent to absorb moisture from liquid body exudates including urine, menses, blood, etc., away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs, and left in place to absorb insults as well as to contain fecal waste.

For articles where the attachment is refastenable, such as diapers and some training pants, pop-opens (separation of the fasteners) can sometimes occur as a result of stresses placed on the attachment by movement of the wearer. For example, and particularly for absorbent articles employing only one fastening system, as an infant or other wearer of the absorbent article moves about (e.g., crawls, walks, runs, bends, etc.) the shear stress placed on the fastening system due to the infant's movement may cause fastening tabs or the like to loosen or even come unfastened completely, resulting in an absorbent article which tends to leak, sag, or fall off of a wearer.

Accordingly, some known absorbent articles comprise more than one fastening system and/or fasteners to reduce the likelihood of the article leaking, sagging, falling off the user, etc. For example, FIGS. 1 and 2 illustrates a known diaper, indicated generally at 10, comprising two fastening systems: a primary fastening system and a secondary fastening system. FIG. 1 depicts the diaper 10 in an unfolded and laid flat condition to show an outer cover 32 of the diaper which faces away from a wearer when the diaper is worn. The diaper 10 has a longitudinal direction 12 and a lateral direction 14.

In the longitudinal direction 12, the diaper 10 defines a front portion 16, a back portion 18, and a crotch portion 20 extending between and connecting the front portion and the back portion. The diaper 10 also includes a bodyside liner 30 (facing away from the view depicted in FIG. 1), and an absorbent core 34 located between the bodyside liner and the outer cover 32. The diaper 10 has opposite longitudinal side edges 28 that extend between a back waist edge 38 and a front waist edge 40. The diaper 10 also includes a pair of longitudinally-extending leg cuffs 36. The leg cuffs 36 may be adapted to fit about the legs of a wearer in use and serve as a mechanical barrier to the lateral flow of body exudates.

The back portion 18 of the diaper 10 includes a pair of back ears, indicated generally at 22. Each ear 22 includes a primary first fastening component 24 as part of the primary fastening system used to secure the diaper 10 around the waist of a wearer. The primary fastening system also comprises a primary second fastening component 76 for selectively receiving and fastening to the primary first fastening components 24. For example, the diaper 10 can be selectively moved from an unfastened configuration (as seen in FIG. 1) to a fastened or wear configuration by attaching the back waist region 18 (and more specifically the back ears 22) to the front waist region 16 to define a three-dimensional wear configuration of the diaper having a waist opening and a pair of leg openings (as seen in FIG. 2). More particularly, the diaper 10 can be selectively moved from the unfastened configuration to the wear configuration by fastening the primary first fastening components 24 to the primary second fastening components 76 as is well known in the art.

The diaper 10 also includes a secondary fastening system comprising secondary first fastening components 26 and secondary second fastening components 78. For example, the illustrated diaper 10 comprises a pair of secondary first fastening components 26 as part of the front portion 16 of the diaper, with a secondary second fastening component 78 provided on each back ear 22. In such configurations, when the diaper 10 is moved to the wear configuration, the secondary first fastening components 26 engages the back portion 18 of the diaper (and more particularly, the secondary second fastening components 78 provided on the back ears 22) such that both the primary fastening system and the secondary fastening system secure the diaper around the waist of a wearer.

However, providing the secondary first fastening components 26 on the diaper 10 may pose drawbacks when the diaper is worn. For example, they may cause irritation to a wearer (because, e.g., each fastener may rub against the wearer's leg during wearing of the diaper). There is a need, therefore, for a cost-effective and improved fastening system provided on an absorbent article which provides for increased protection against leakage and secure attachment of the absorbent article without the associated discomfort discussed above.

SUMMARY

In one aspect, an absorbent article includes an absorbent assembly having longitudinally opposite ends, transversely opposite sides, a front waist region, a back waist region, and a crotch region extending longitudinally between and interconnecting the front and back waist regions, a liquid permeable inner layer for facing a wearer, and an outer layer for facing away from the wearer. An absorbent body is disposed between the inner and outer layers. At least one of the inner layer and outer layer defines the longitudinally opposite ends and transversely opposite sides of the absorbent assembly. The absorbent body has a pair of longitudinally extending sides and a pair of transversely extending ends, each of the longitudinally extending sides of the absorbent body being spaced inward from a respective one of the transversely opposite sides of the absorbent assembly. A pair of ears extend transversely outward from the opposite sides of the absorbent assembly in the back waist region, each of the ears including a primary first fastening-component that is selectively engagable with a primary second fastening-component in the front waist region of the absorbent assembly in a wear configuration of the article. Further included is a pair of spaced-apart secondary first fastening-components disposed on the outer layer in the front waist region of the absorbent assembly, each of the secondary first fastening-components being selectively engageable with a respective one of the secondary second fastening-components in a wear configuration of the article. The secondary first fastening-components fit into respective fastener regions, each fastener region defined by an outline surrounding the secondary first-fastening components, wherein each outline has a waist edge and an opposite leg edge connected by an outer edge and an inner edge. The wherein the length of the outline outer edge is shorter than the length of its inner edge. The primary first fastening-components do not overlap the secondary first-fastening components in a wear configuration of the article.

In another aspect, an absorbent article includes an absorbent assembly having longitudinally opposite ends, transversely opposite sides, a front waist region, a back waist region, and a crotch region extending longitudinally between and interconnecting the front and back waist regions, a liquid permeable inner layer for facing a wearer, an outer layer for facing away from the wearer. An absorbent body is disposed between the inner and outer layers, at least one of the inner layer and outer layers defining the longitudinally opposite ends and transversely opposite sides of the absorbent assembly. The absorbent body has a pair of longitudinally extending sides and a pair of transversely extending ends, each of the longitudinally extending sides of the absorbent body being spaced inward from a respective one of the transversely opposite sides of the absorbent assembly. A pair of ears extend transversely outward from the opposite sides of the absorbent assembly in the back waist region, each of the ears comprising a primary first fastening-component that is selectively engagable with a primary second fastening-component in the front waist region of the absorbent assembly in a wear configuration of the article. A pair of spaced-apart secondary first fastening-components are disposed on the outer layer in the front waist region of the absorbent assembly, each of the secondary first fastening-components being selectively engageable with a respective one of the secondary second fastening-components in a wear configuration of the article. The secondary first fastening-components are defined by at least two islands, a waist-region island having a first area, and a leg-region island having a second area. The first island area is larger than the second island area. The primary first fastening-components do not overlap the secondary first-fastening components in a wear configuration of the article.

In yet another aspect, an absorbent article includes an absorbent assembly having longitudinally opposite ends, transversely opposite sides, a front waist region, a back waist region, and a crotch region extending longitudinally between and interconnecting the front and back waist regions, a liquid permeable inner layer for facing a wearer, an outer layer for facing away from the wearer. An absorbent body is disposed between the inner and outer layers, at least one of the inner layer and outer layer defining the longitudinally opposite ends and transversely opposite sides of the absorbent assembly. The absorbent body has a pair of longitudinally extending sides and a pair of transversely extending ends, each of the longitudinally extending sides of the absorbent body being spaced inward from a respective one of the transversely opposite sides of the absorbent assembly. A pair of ears extend transversely outward from the opposite sides of the absorbent assembly in the back waist region, each of the ears comprising a primary first fastening-component that is selectively engagable with a primary second fastening-component in the front waist region of the absorbent assembly in a wear configuration of the article. A pair of spaced-apart secondary first fastening-components are disposed on the outer layer in the front waist region of the absorbent assembly, each of the secondary first fastening-components being selectively engageable with a respective one of the secondary second fastening-components in a wear configuration of the article. The secondary first fastening-components are defined by rows of islands disposed within a rectangular region having a waist edge and an opposite leg edge connected by an outer edge and an inner edge. Each row of islands is comprised of one island and aligned with the inner edge. The row of islands adjacent the leg edge is shorter in a transverse direction than an adjacent row of islands. The primary first fastening-components do not overlap the secondary first-fastening components in a wear configuration of the article.

BRIEF DESCRIPTION OF THE DRAWINGS

FIG. 18 is a top plan view of a prior art secondary first fastener.

FIG. 19 is a top plan view of the secondary first fastener shown in FIGS. 3-5.

FIG. 22 is a top plan view of the secondary first fastener shown in FIGS. 12-14.

FIG. 23 is a top plan view of the secondary first fastener shown in FIGS. 15-17.

Corresponding reference characters indicate corresponding parts throughout the several views of the drawings.

DETAILED DESCRIPTION OF THE DRAWINGS

According to some aspects of the disclosure, an absorbent article is provided which overcomes at least some of the deficiencies of the conventional diapers described above. More particularly, according to some aspects of the disclosure, the absorbent article includes a secondary fastening system in order to securely attach the absorbent article around the waist of a wearer, but which comprises improved pliability over known fastening systems such that the absorbent article remains securely fastened even as the wearer crawls, walks, runs, bends, etc. The secondary fastening system may be constructed of suitable materials and disposed in a suitable position relative to other components of the absorbent article such that the absorbent article may be readily packaged or used without the drawbacks of the known diapers discussed above.

Figure 3:
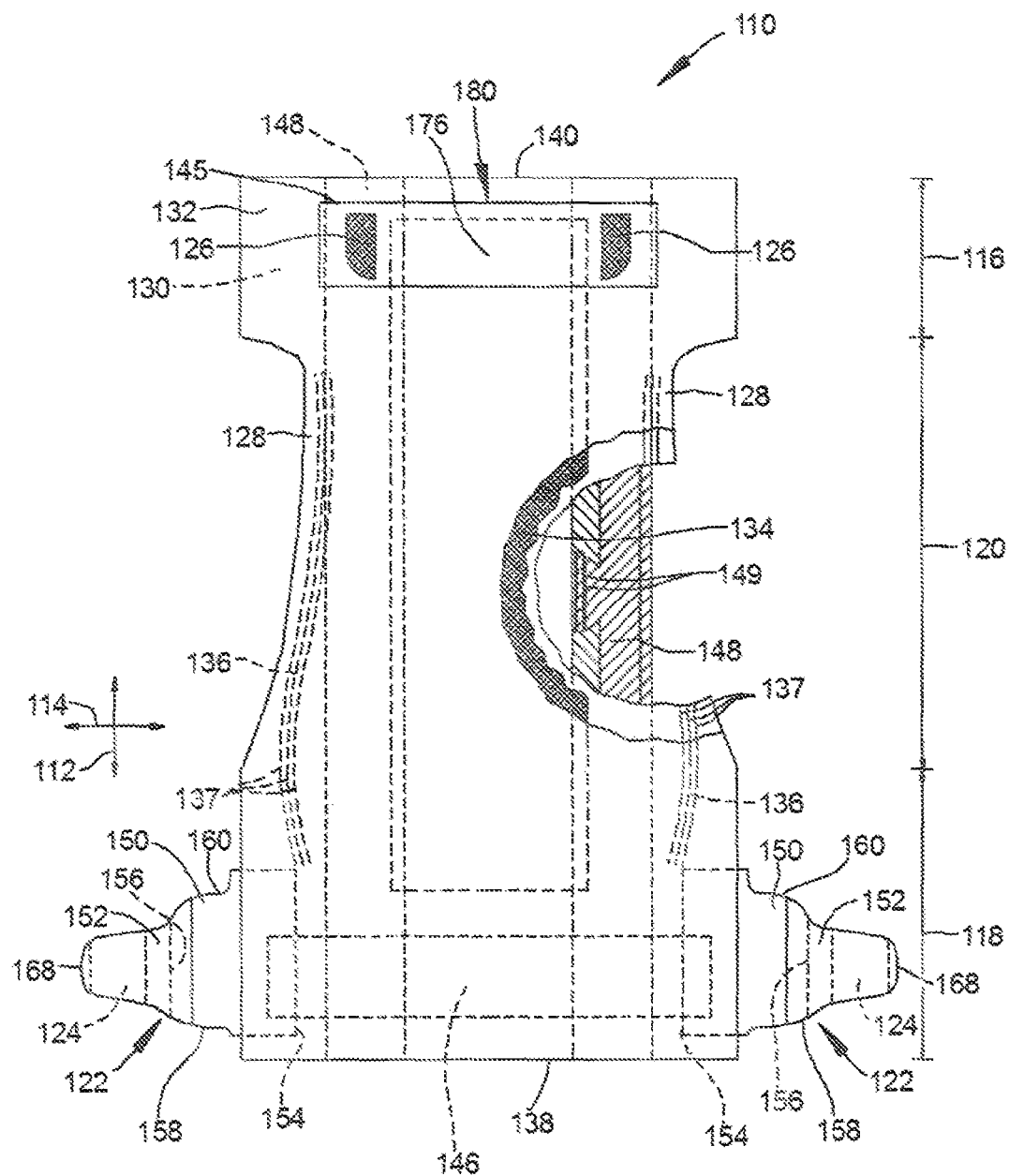
FIG. 3 is a top plan view of a diaper according to one embodiment of the present disclosure in an unfolded and laid flat condition to show an outer surface of the diaper which faces away from the wearer when the diaper is worn.
Figure 4:
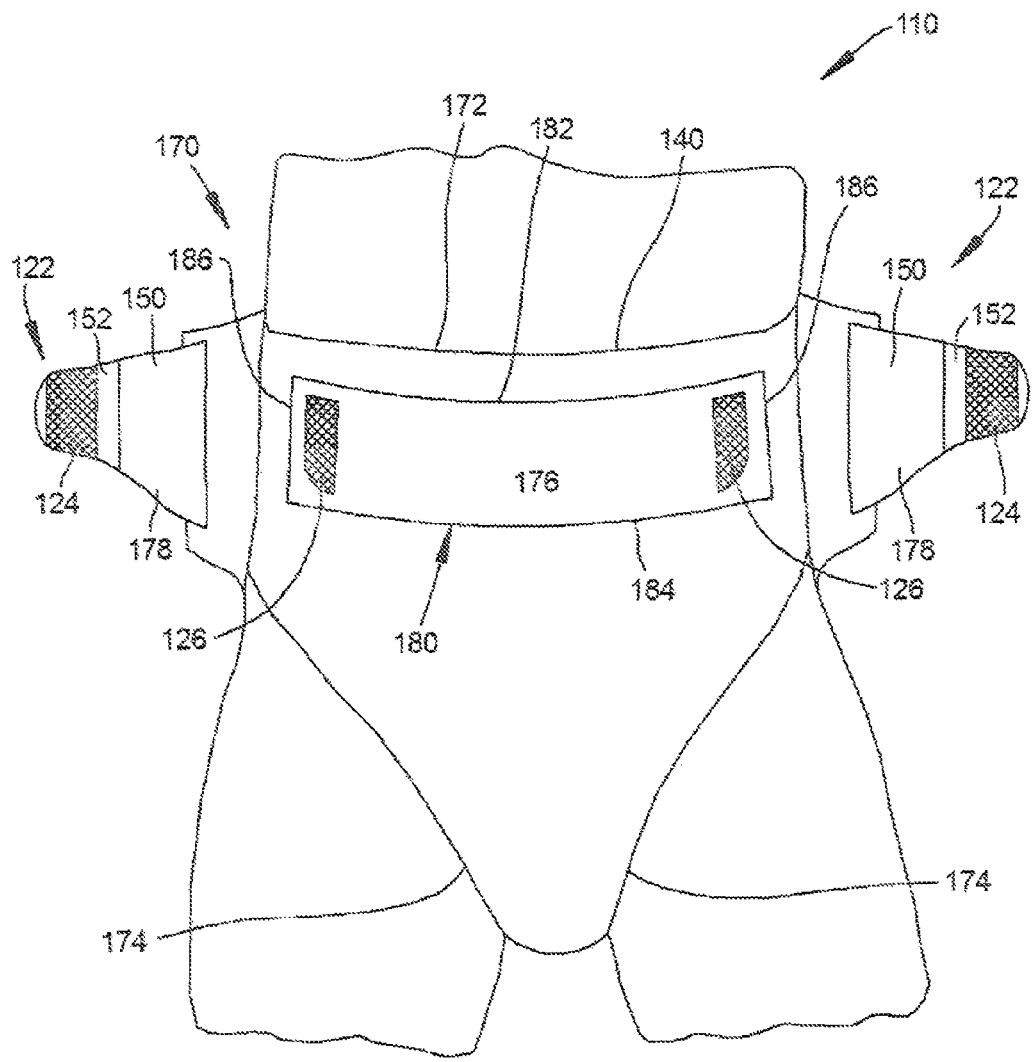
FIG. 4 is a front view of the diaper of FIG. 3 in a wear configuration, with the fastening system not fastened.
Figure 5:
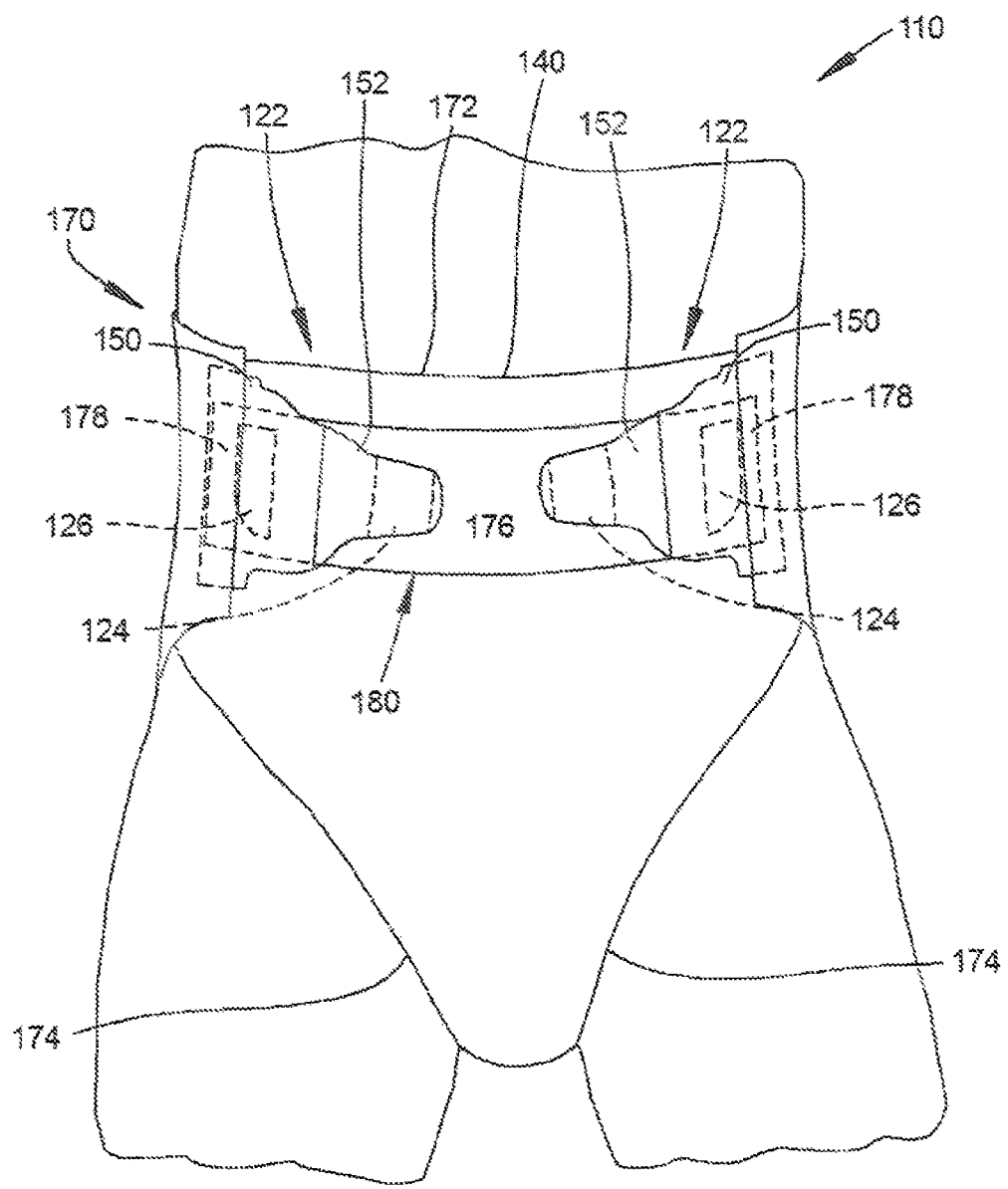
FIG. 5 is a front view of the diaper of FIG. 3 in a wear configuration with the fastening system fastened.

These features will become more apparent with reference to the accompanying drawings. FIG. 3 illustrates one suitable embodiment of a diaper (broadly, "an absorbent article"), indicated generally at 110, in an unfolded and laid flat condition to show an outer surface of the diaper which faces away from the wearer when the diaper is worn (FIGS. 4 and 5). Portions of the diaper 110 illustrated in FIG. 3 are cut away to illustrate underlying structures. The diaper 110 has a longitudinal direction 112 and a lateral direction 114. While the present description will be made in the context of a diaper 110, it should be understood that the present disclosure is also applicable to other personal care absorbent articles, such as adult incontinence garments, children's training pants, swim pants, and the like.

In one suitable embodiment, the diaper 110 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the diaper 110 can be reusable. That is, the diaper 110 can be intended for multiple uses without departing from some aspects of this disclosure.

Figure 26:
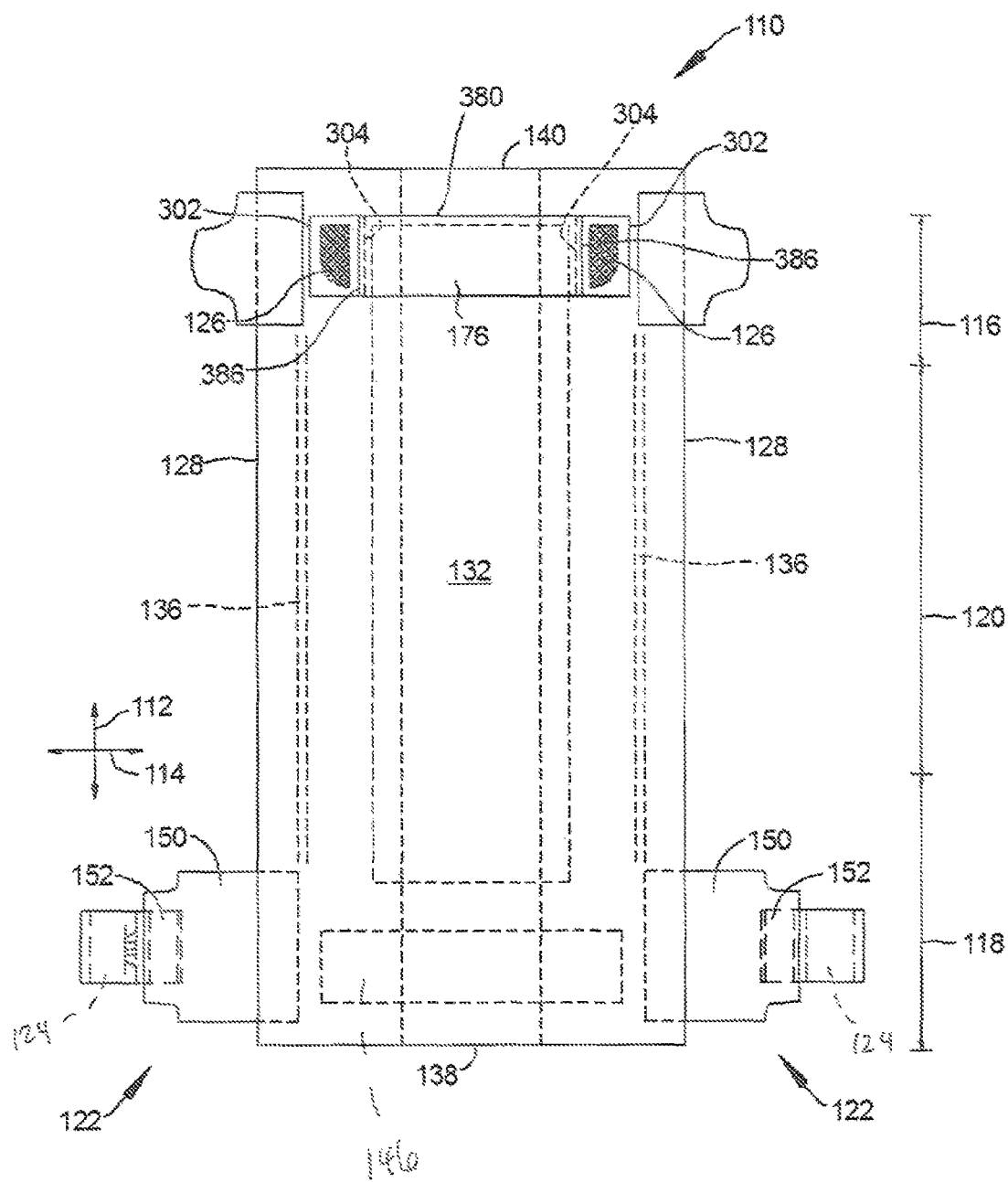
FIG. 26 is a top plan view of a diaper according to another embodiment in an unfolded and laid flat condition to show an outer surface of the diaper which faces away from the wearer when the diaper is worn, wherein the secondary first fastener is located on a carrier.

In the longitudinal direction 112, the diaper 110 defines a front portion 116, a back portion 118, and a crotch portion 120 extending between and connecting the front portion and the back portion. The diaper 110 includes a bodyside liner 130, an outer cover 132, and an absorbent core 134 located between the bodyside liner and the outer cover. The bodyside liner 130, outer cover 132 and absorbent core 134 collectively define an absorbent assembly. The absorbent assembly can be any suitable shape including, for example, generally I-shaped as illustrated in FIGS. 3, 6, 9, 12 and 15, or generally rectangular as illustrated in FIG. 26. As used herein, reference to the front portion 116 refers to that part of the diaper 110 which is generally located on the front of a wearer when in use. Reference to the back portion 118 refers to the portion of the diaper 110 generally located at the back of the wearer when in use, and reference to the crotch portion 120 refers to that portion which is generally located between the legs of the wearer when in use.

In the illustrated embodiment, the back portion 118 includes a straight back waist edge 138 and the front portion 116 includes a straight front waist edge 140. As used herein, "straight edge" refers to edges that are substantially free from curves, bends, angles, notches, or irregularities. It is understood, however, that the back waist 138 and the front waist 140 may be cut in any suitable shape as are known in the art (e.g., arcuate). As seen in FIG. 3, the diaper 110 has opposite longitudinal side edges 128 that extend between the back waist edge 138 and the front waist edge 140. In the illustrated embodiment, each of the side edges 128 include an arcuate portion for defining a portion of a leg opening during wear of the diaper 110.

The bodyside liner 130 of the diaper 110, as illustrated in FIG. 3, defines a body facing surface that is intended to be worn adjacent and in directed contact with the body of the wearer. The bodyside liner 130 is suitably compliant, soft feeling and nonirritating to the wearer's skin. The bodyside liner 130 is less hydrophilic than the absorbent core 134 and sufficiently porous to be liquid permeable. The bodyside liner 130 can be manufactured from a wide selection of suitable web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 130 is suitably adapted to isolate the wearer's skin from liquids and moisture held by the absorbent core 134.

The outer cover 132 of the diaper 110, which is illustrated in FIG. 3, defines a garment facing surface which is intended to be worn adjacent the clothing of the wearer. In one suitable embodiment, the outer cover 132 is a polyethylene film. In another suitable embodiment, the outer cover 132 comprises a woven or non-woven fibrous web layer which has been totally or partially constructed or treated to impart a desired level of liquid impermeability to selected regions of the outer cover that are adjacent or proximate the absorbent core 134. For example, a clothlike outer cover may be composed of polypropylene spunbond fabric which is laminated and thermally bonded to a stretch-thinned polypropylene film. The outer cover 132 may include a microporous, "breathable" material which permits vapors to escape from diaper 110 while still preventing liquid exudates from passing through. For example, the outer cover 132 may be composed of a microporous polymer film or a nonwoven fabric which has been coated or otherwise treated to impart a desired level of liquid impermeability. The outer cover 132 can also be embossed or otherwise provided with a matte finish to exhibit a more aesthetically pleasing appearance.

The bodyside liner 130 and the outer cover 132 are generally joined in facing relationship with the absorbent core 134 located therebetween. The bodyside liner 130 and the outer cover 132 can be joined to each other around the outer periphery of the diaper 110 by any means known to those skilled in the art such as adhesive bonds, ultrasonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

As mentioned above, the absorbent core 134 is positioned between the bodyside liner 130 and the outer cover 132. The absorbent core 134 is generally conformable and capable of absorbing and retaining liquid body exudates. The absorbent core 134 can include superabsorbent material, staple fibers, binder fibers, and the like, and combinations thereof as is known in the art. The absorbent core 134 may have any of a number of shapes and sizes. For example, the composite absorbent core 134 may be rectangular, I-shaped, or T-shaped. The size and absorbent capacity of the absorbent core 134 should be compatible with the size of the intended wearer and the fluid loading imparted by the intended use of the diaper.

In one suitable embodiment, the diaper 110 may include a surge portion (not shown) disposed between the absorbent core 134 and the bodyside liner 130. The surge portion serves to quickly collect and temporarily hold liquids discharged by the wearer and then release the liquids to the absorbent core 134. Various woven and nonwoven materials can be used to construct the surge portion. For example, the surge portion may be a layer of a spunbonded or meltblown web of polyolefin fibers. The surge portion may also be a bonded carded web of natural and synthetic fibers. The surge portion may be a substantially hydrophobic material and, optionally, can be treated with a surfactant or otherwise to impart a desired level of wettability and hydrophilicity.

The diaper 110 includes a pair of elasticized, longitudinally-extending leg cuffs 136. The leg cuffs 136 are adapted to fit about the legs of a wearer in use and serve as a mechanical barrier to the lateral flow of body exudates. In one suitable embodiment, the leg cuffs 136 can be formed by portions of the outer cover 132, and/or bodyside liner 130, which extend beyond the longitudinal sides of the absorbent core 134. In another suitable embodiment, the leg cuffs 136 can be formed from separate materials (e.g., stands of leg elastics) joined to the outer cover 132 and/or the bodyside liner 130.

The diaper 110 may further include a front waist elastic (not shown) and/or a back waist elastic 146. In the illustrated embodiment, for example, the diaper 110 has a back waist elastic 146 but not a front waist elastic. The back waist elastic 146 is arranged to draw and hold the diaper 110 against the wearer, particularly against the waist of the wearer, as will be more fully discussed.

Figure 1:
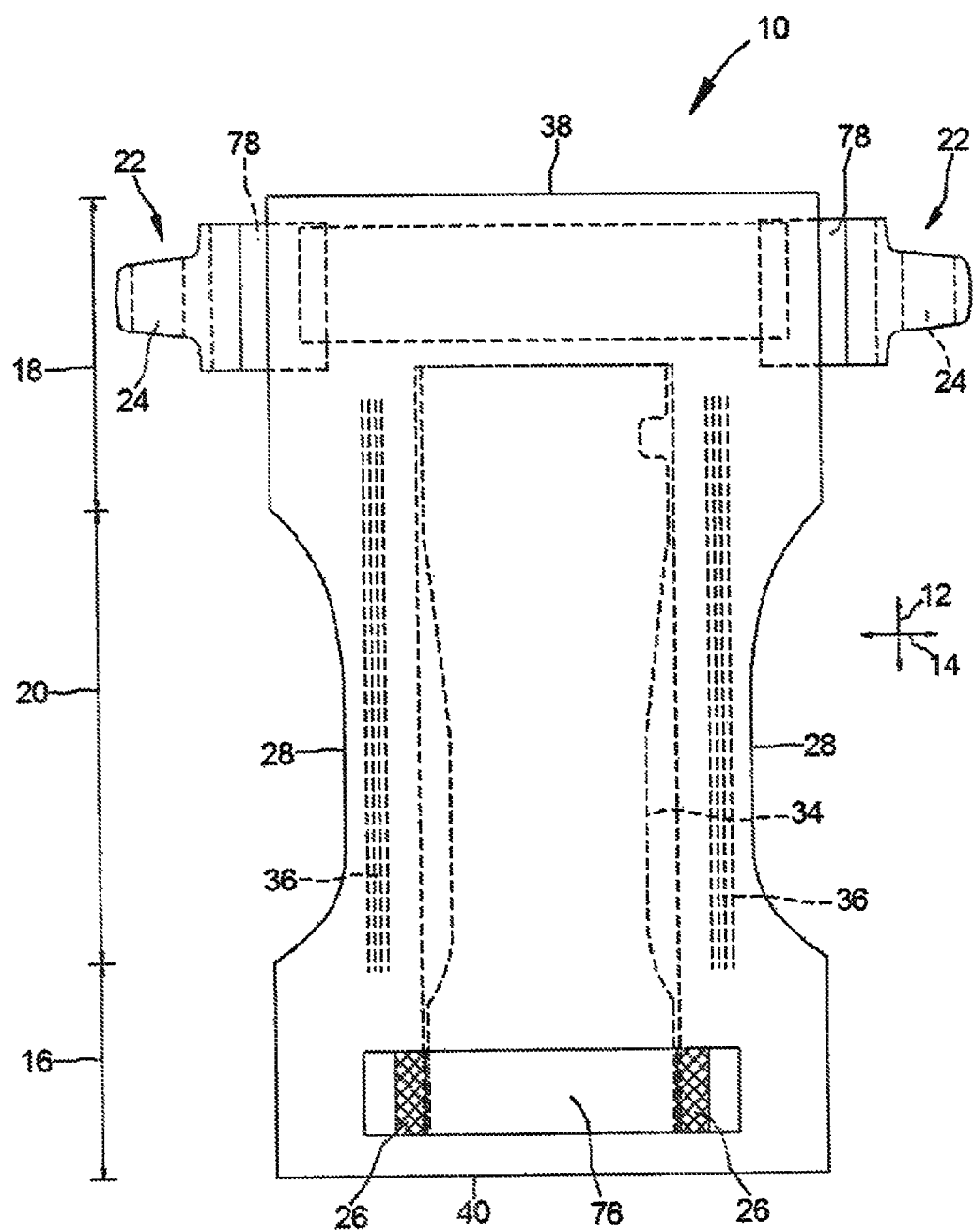
FIG. 1 is a top plan view of a known diaper in an unfolded and laid flat condition to show an outer surface of the diaper which faces away from the wearer when the diaper is worn.

Materials suitable for use in forming leg cuffs 136 and/or waist elastics 146 are known to those skilled in the art. Examples of such materials are strands or ribbons of a polymeric, elastomeric material which are adhered to the diaper 110 in a stretched position, or which are attached to the diaper while the diaper is pleated, such that elastic constrictive forces are imparted to the diaper. The leg cuffs 136 and/or waist elastics 146 may have any configuration which provides the desired performance. The leg cuffs 136 may be generally straight (as illustrated in FIGS. 1 and 26) or optionally curved (as illustrated in FIGS. 3, 6, 9, 12 and 15 to more closely fit the contours of the legs of the wearer. As used herein, "elastic," "elastomeric," and the like refer to the ability of a material or composite to be elongated by at least about 50 percent and upon relaxation to return to within at least 50 percent of its original length.

The leg cuffs 136 and/or waist elastics 146 may be attached to the diaper 110 in any way known to those skilled in the art. For example, the leg cuffs 136 and/or waist elastics 146 may be joined to the diaper 110 by ultrasonic bonding, thermal bonding, adhesive bonding, and the like, and combinations thereof.

The diaper 110 may also include a pair of containment flaps 148 that extend longitudinally along the diaper and are adapted to provide a barrier to the lateral flow of body exudates. The containment flaps can be connected to the bodyside liner 130 or other components as is well known in the art. Suitable configurations of the containment flaps 148 are described, for example, in U.S. Pat. No. 5,599,338 issued Feb. 4, 1997, to K. Enloe, the entirety of which is incorporated herein by reference.

As seen in FIG. 3, the back portion 118 of the diaper includes a pair of back ears, indicated generally at 122. In one suitable embodiment, the back ears 122 can be formed from extensions of the bodyside liner 130, the outer cover 132, or combinations of both the bodyside liner and the outer cover. In another suitable embodiment, and as illustrated in FIGS. 3-5, the back ears 122 can be formed as separate components and attached to the bodyside liner 130, the outer cover 132, or both the bodyside liner and the outer cover as is known in the art. In the illustrated embodiment, the back ears 122 are attached to the body-facing surface of the bodyside liner 130 such that the attached portion of the ears 122 are disposed between the wearer's body and bodyside liner when the diaper 110 is worn.

In one suitable embodiment, each of the back ears 122 includes an elastomeric portion 150, a non-elastomeric portion 152, and a primary first fastening component 124 mounted to the non-elastomeric portion (FIG. 3). Each of the elastomeric portions 150 has a proximal edge 154, an opposed distal edge 156, an upper edge 158, and a lower edge 160. The proximal edge 154 of each of the elastomeric portions 150 is spaced inward from the respective side edge 128 of the diaper 110 such that a portion of the elastomeric portion overlaps the bodyside liner 130. The part of each of the elastomeric portions 150 overlapping the bodyside liner 130 is bonded (e.g., adhesive bonding, thermal bonding, both thermal and adhesive bonding) to at least the bodyside liner. In another suitable embodiment, the elastic component 150 may be eliminated and the entire back ear 122 may be constructed from the non-elastic component 152.

In the embodiment illustrated in FIG. 3, the proximal edge 154 and the distal edge 156 of each of the elastomeric portions 150 are generally parallel with respect to each other, and both are straight (i.e., linear). In one suitable embodiment, the proximal edge 154 has a length from about 2 inches (5.1 centimeters) to about 7 inches (17.8 centimeters), preferably from about 3 inches (7.6 centimeters) to about 6 inches (15.2 centimeters), and more preferably from about 3.5 inches (8.9 centimeters) to about 5.5 inches (14.0 centimeters). The distal edge 156 has a length from about 0.25 inch (0.635 centimeter) to about 6 inches (15.24 centimeters), and preferably from about 1 inch (2.54 centimeters) to about 3 inches (7.6 centimeters). Further, the ratio of the length of the distal edge 156 to the proximal edge 154 is suitably from about 1:28 to about 3:4, and, and preferably from about 1:10 to about 2:3, and more preferably from about 1:4 to about 1:2.

Each of the illustrated elastomeric portions 150 includes an arcuate third segment 166 interconnecting the second segments 164 to the respective distal edge 156. In the illustrated embodiment, the third segments 166 are generally mirror images of each other. It is understood, however, that the third segments 166 can have any suitable shape and that the third segments of the upper edges 158 can have a shape that is different that the shape of the third segments of the lower edges 160.

Figure 2:
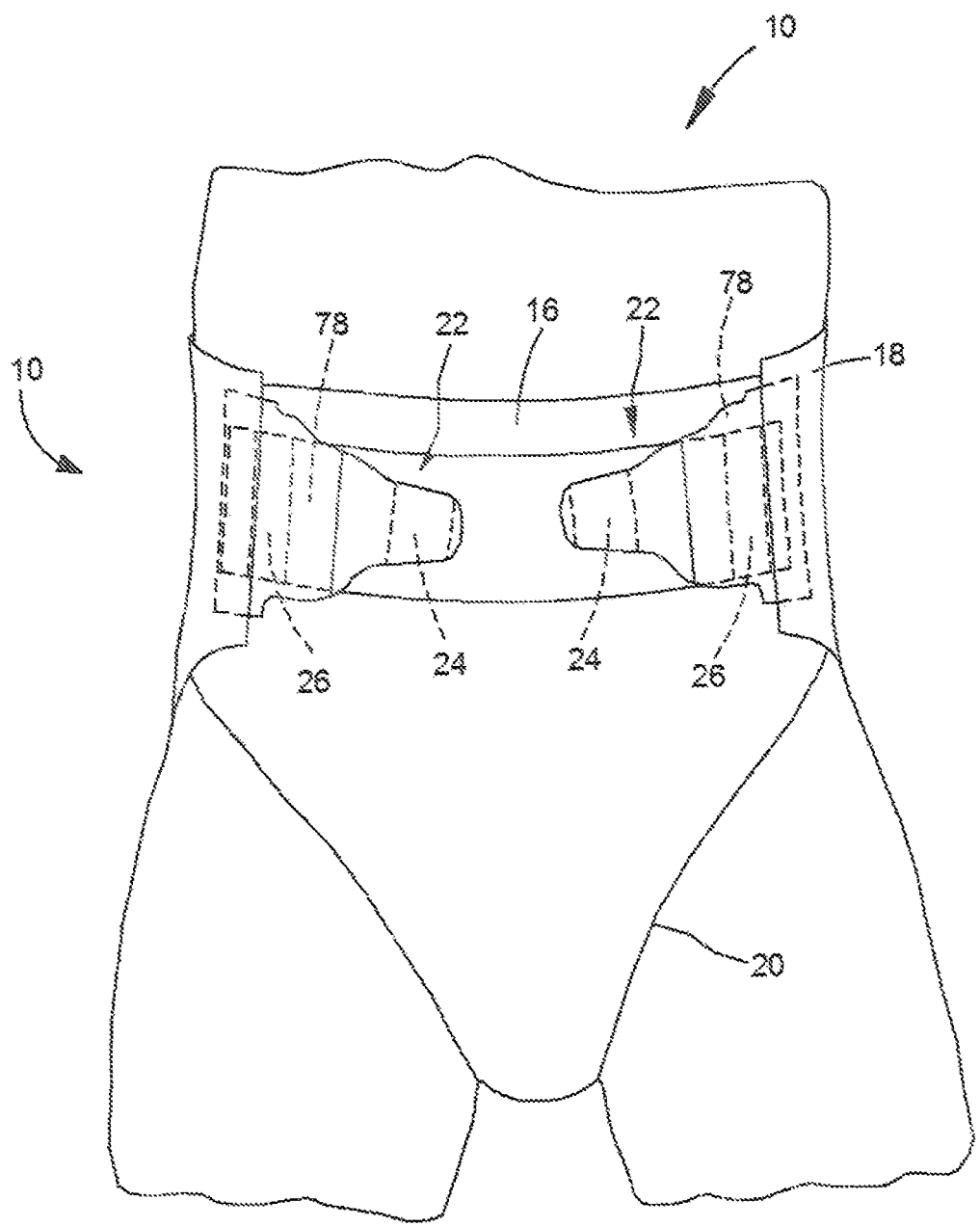
FIG. 2 is a front view of the diaper of FIG. 1 in a wear configuration with the fastening system not fastened.

The elastomeric portions 150 of the back ears 122 can be formed from any type of elastomeric material capable of performing as described herein. In one suitable embodiment, the elastomeric material will be stretchable in at least one direction (e.g., in the lateral direction 114 of the diaper 110 as viewed in FIG. 3) and alternatively, the elastomeric material will be stretchable in two directions (e.g., in both the longitudinal direction 112 and the lateral direction of the diaper as viewed in FIGS. 2 and 3). Suitably when the elastomeric material is stretchable in a single direction, the stretch direction of the elastomeric material will be oriented so as to provide elastomeric forces which tend to pull the front and rear portions of the article towards one another such that the article is maintained about the waist of a wearer.

In one suitable embodiment, the elastomeric material from which the elastomeric portions 150 of the back ears 122 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material may be an inherently elastomeric material, that is, one which is formed in an elastomeric state, or may be rendered elastomeric through processing subsequent formation. For example, the elastomeric material may be heat or pressure activated. The elastomeric portions 150 of the back ears 122 can be formed from a stretch-bonded-laminate (SBL) material, a neck-bonded-laminate (NBL) material, an elastomeric film, an elastomeric foam material, or the like.

Each of the non-elastomeric portions 152 of the back ears 122 is attached to a respective one of the elastomeric portions 150, and the primary first fastening components 124 (such as a hook material) are in turn disposed on the non-elastomeric portions. As illustrated in FIG. 3, the non-elastomeric portions 152 of the back ears 122 extend in part transversely outward of the respective elastomeric portion 150 and the primary first fastening component 124 of each of the non-elastomeric portions are configured for engaging a loop component disposed in the front waist region 116 of the diaper 110 in the wear configuration, as will be discussed more fully.

As seen best in FIG. 3, each of the illustrated non-elastomeric portions 152 further comprise a grip region 168 transversely outward of the primary first fastening component 124 for use in manually gripping and manipulating the non-elastomeric portion and more broadly the respective back ear 122 relative to the diaper 110. The grip region 168 is non-attachable to the diaper 110. The term "non-attachable" as used in this instance means that the grip region 168 is not releasably or otherwise removably attachable to the diaper 110. In one embodiment, the grip region 168 extends transversely outward from the respective primary first fastening component 124 a distance of at least about 1 mm, such as in the range of about 1 mm to about 10 mm to provide sufficient unattached material for readily gripping and pulling on the non-elastomeric portion 152.

The diaper 110 can be selectively moved from the unfastened configuration, as illustrated in FIG. 3, to a fastened or wear configuration as illustrated in FIG. 5, by attaching the back waist region 118 (and more specifically the back ears 122) to the front waist region 116 using an article fastening system 170 to define a three-dimensional wear configuration of the diaper having a waist opening 172 and a pair of leg openings 174. Although the diaper 110 shows the back waist region 118 (and more specifically the back ears 122) overlapping the front waist region 116 upon connection thereto, which is convenient, the diaper can also be configured so that the front waist region overlaps the back waist region when connected.

According to some embodiments, the article fastening system 170 comprises a primary fastening system and a secondary fastening system. The primary fastening system comprises the primary first fastening components 124 disposed on the non-elastomeric portions 152 of the back ears 122 and at least one corresponding primary second fastening component 176 which is adapted for refastenable engagement to the primary first fastening components. In one suitable embodiment, an outer surface of each of the primary fastening components 124, 176 comprises a plurality of engaging elements. More specifically, the engaging elements of the primary first fastening components 124 are adapted to repeatedly engage and disengage corresponding engaging elements of the primary second fastening components 176 to releasably secure the diaper 110 in its wear configuration.

The primary fastening components 124, 176 may comprise any refastenable fasteners suitable for absorbent articles, such as adhesive fasteners, cohesive fasteners, mechanical fasteners, or the like. In one suitable embodiment, the primary fastening components 124, 176 comprise mechanical fastening components, such as hook and loop fasteners. For example, suitable hook and loop components can be provided by interlocking geometric shaped materials. As used herein, "hook" broadly refers to any suitable mechanical fastener adapted to engage loop components including, e.g., hooks, bulbs, mushrooms, arrowheads, balls on stems, stems, structures having stems that engage foam such as open cell foam or the like, etc. Other suitable mechanical fastening components include male and/or female mating components, buckles, snaps, or the like. In the illustrated embodiment, the primary first fastening components 124 comprise hook fasteners and the primary second fastening components 176 comprise a complementary loop fastener disposed on the outer surface of the outer cover 132. Alternatively, the primary first fastening components 124 may comprise loop fasteners and the primary second fastening components 176 may comprise complementary hook fasteners.

The shape, density, and polymer composition of the hooks and loops may be selected to obtain the desired level of engagement between the primary fastening components 124, 176. A more aggressive hook material may comprise a material with a greater average hook height and/or a greater percentage of directionally-aligned hooks.

In some embodiments, the outer facing surface of the outer cover 132 of the diaper 110 is suitably constructed to define the primary second fastening component 176, which is a loop fastener. That is, the outer cover 132 itself can be formed of a material that defines the primary second fastening component 176 (e.g., vertical filament laminate (VFL) or other suitable material).

In another suitable embodiment, and as illustrated in FIG. 4, the primary second fastening component 176 can be formed as a separate component and attached to the outer surface of the diaper's outer cover 132. More specifically, a strip, indicated generally at 180, comprising loop fastening material is attached to the front waist region 116 of the diaper. The strip 180 comprises an upper edge 182, a lower edge 184, and a pair of side edges 186 connecting the upper and lower edges 182, 184. The upper edge 182 is spaced from the front waist edge 140 and the side edges 186 are spaced from the respective side edges 128 of the diaper 110.

The secondary fastening system of the article fastening system 170 comprises secondary first fastening components 126 and secondary second fastening components 178. The secondary first fastening components 126 are disposed on the front portion 116 of the diaper 110 and are adapted for refastenable engagement to at least one corresponding secondary second fastening component 178 (e.g., the elastomeric portion 150 of the back ears 122). As best seen FIGS. 3 and 4, in some embodiments, the strip 180 may comprise the pair of spaced-apart secondary first fastening components 126.

In the illustrated embodiment of FIG. 4, the secondary first fastening components 126 comprise hook fasteners and are configured to engage the secondary second fastening components 178 in the wear configuration of the diaper 110. Again, as used herein "hook" fasteners refers broadly to any suitable mechanical fastener adapted to engage loop components including, e.g., hooks, bulbs, mushrooms, arrowheads, balls on stems, stems, structures having stems that engage foam such as open cell foam or the like, etc. In one embodiment, the secondary first fastening components 126 may be constructed of polyethylene or other suitable polymer blends. In one suitable embodiment, the elastomeric portions 150 of the back ears 122 are constructed so at least the inner surfaces of the elastomeric portions define the secondary second fastening components 178 in the form of loop fastening components (i.e., the elastomeric portions and the respective secondary second fastening components are formed integrally). The elastomeric portions 150 in one suitable embodiment can be constructed of NBL material so that the elastomeric portions itself defines a loop fastening component. In another suitable embodiment, the elastomeric portions 150 can be constructed of VFL material so that the elastomeric portions itself defines a loop fastening component. It is understood, however, that the secondary second fastening components 178 may be formed separate from the elastomeric portions 150 and attached thereto, such as by adhesive, thermal bonds, ultrasonic bonds, pressure bonds, or other suitable techniques without departing from the scope of this disclosure.

In other suitable embodiments, the secondary first fastening components 126 may comprise loop fasteners and the secondary second fastening components 178 may comprise hook fasteners. Further, in some embodiments the secondary first fastening components 126 may be a single, integral fastener. For example, in one suitable embodiment the secondary first fastening components 126 may be a single, hook fastener, and the secondary second fastening components 178 may be loop fasteners.

In one suitable embodiment, the strip 180 comprising both the secondary first fastening components 126 and the primary second fastening component 176. In one such embodiment where the primary second fastening component 176 comprises a loop material and the secondary first fastening component 126 comprises a hook material, the strip 180 may be a suitable loop material (forming the primary second fastening component), and then the hook material may be extruded onto the loop material at two or more locations forming the secondary first fastening components.

In another suitable embodiment, the secondary first fastening components 126 can be formed separate from the primary second fastening component 176. In such an embodiment, the primary second fastening component 176 can be formed to define the strip 180 and the secondary first fastening components 126 can be attached in overlaying relationship with portions of the primary second fastening component. In such embodiments, the secondary first fastening components 126 may be attached to the strip 180 and/or the primary second fastening component 176 using any suitable means known to those skilled in the art, including, e.g., adhesive bonds, ultrasonic bonds, thermal bonds, pressure bonds, and the like, and combinations thereof.

In some embodiments, the secondary first fastening components 126 may be attached to the diaper 110 and/or the strip 180 after the strip has been attached to the diaper 110. For example, in one suitable embodiment the strip 180 may be first bonded to the diaper 110 using any suitable means as discussed, and then the secondary first fastening components 126 may be bonded to or extruded on the strip. In other embodiments, the strip 180 comprising both the secondary first fastening components 126 and primary second fastening components 176 can be attached to the diaper 110 as one single unit.

According to some embodiments, the secondary first fastening components 126 and/or the strip 180 may be sufficiently bonded to the diaper 110 such that a shear force exerted on the secondary first fastening components and/or the strip during use of the diaper does not cause the secondary first fastening components and/or the strip to loosen or completely disengage from the diaper. For example, in some embodiments an improved adhesive or the like can be used such that the secondary first fastening components 126 and/or the strip 180 remain securely fastened to, e.g., the outer cover despite the forces exerted on the fastening system 170 during use. In such embodiments, the diaper 110 may be less prone to pop-opens and the edges of the secondary first fastening components 126 and/or the strip 180 may remain flush with the outer cover 132 thus reducing irritation during wear which may otherwise be caused by a loose secondary first fastener and/or a loose strip.

Referring now to FIG. 5, when the diaper 110 is moved to the wear configuration with the primary fastening components 124, 176 engaging one another, the secondary fastening components 126, 178 may also engage one another in order to provide increased stability and leakage protection. For example, because the article fastening system 170 comprises four engagement points, the diaper 110 will be less prone to pop-opens when worn. Further, because the secondary fastening components 126, 178 engage each other closer to a side of a wearer than an engagement point of the primary fastening components 124, 176, the secondary fastening system secures the diaper 110 nearer the wearer's sides and legs thus reducing leakage near the leg openings 174 of the diaper. Still further, and again because the secondary fastening components 126, 178 engage each other near a side of the wearer, the secondary fastening system may provide increased stability, thus reducing the occurrence of, e.g., sagging of the diaper due to movement of the wearer.

Referring now to FIG. 19, shown is an enlargement of the secondary first fastening component 126 shown in FIGS. 3-5. In this particular embodiment, the fastening component 126 can be generally described as an altered rectangle that has one corner removed and replaced by an arcuate edge 403. This fastening component 126 occupies a region 400 that may be located on strip 180 as shown. Specifically, the region 400 is defined by an outline 401 having a straight waist edge 402 and an opposite connecting edge 424 (also coinciding with arcuate edge 403), which are connected together by a straight outer edge 406 and a straight inner edge 408.

The length 410 of the outer edge 406 is shorter than the length 412 of the inner edge 408. Referring also to FIG. 18, this length difference provides at least one advantage to the wearer over that presented by the prior art fastening component 26, that is, there is less opportunity for the fastening component 126 to irritate and/or cause red-marking to the wearer's skin. In addition, the fastening component 126 requires less material than the prior-art fastening component 26.

It is desirable in some embodiments to have the inner edge length 412 of the fastening component 126 shorter than the length 413 of strip 180. This leaves a distance 500 between the fastening component waist edge 402 strip upper edge 182, and a distance 502 between the lowest point of the fasting component connecting edge 424 and strip lower edge 184. This also helps to prevent irritation to the wearer's skin.

Referring to FIG. 5, is should be noted that when the article 110 is in a wear configuration, the primary first fastening components 124 do not overlap the secondary first fastening components 126. This is true for all the embodiments of the fastening system disclosed in FIGS. 3-23.

In the embodiment shown in FIGS. 3-5 and 19, there is a region 400 that contains a single "island" 420. It should be observed that when the waist edge 402 is bisected by a normal axis-line 422, the fastening component 126 area between the outer edge 406 and the axis line 422 is less than the fastening component 126 area between the inner edge 408 and axis line 422. Thus, within region 400, the island 420 has more area on its inner portion than its outer portion.

It should further be observed that there is an obtuse angle 426 formed by the outer edge 406 and a straight line that connects each end of the arc forming arcuate edge 403. This line may be referred to as a leg edge 404. The obtuse angle 426 between leg edge 404 and outer edge 406 may be between about 100 degrees and 150 degrees, or in other embodiments, between 110 and 140 degrees, and in yet other embodiments, between 115 and 130 degrees.

In the various embodiments of the secondary first fastening components 126 shown in FIGS. 6-17 and 19-23, each region 400 contains two or more islands 420. Collectively, the islands 420 form a discontinuous secondary first fastening system.

In the secondary fasting component embodiment shown in FIGS. 6-8 and 20, the islands 420 are a combination of secondary fastening components 126a, 126b, having a side-by-side configuration with respect to the waist edge 402.

Figure 20:
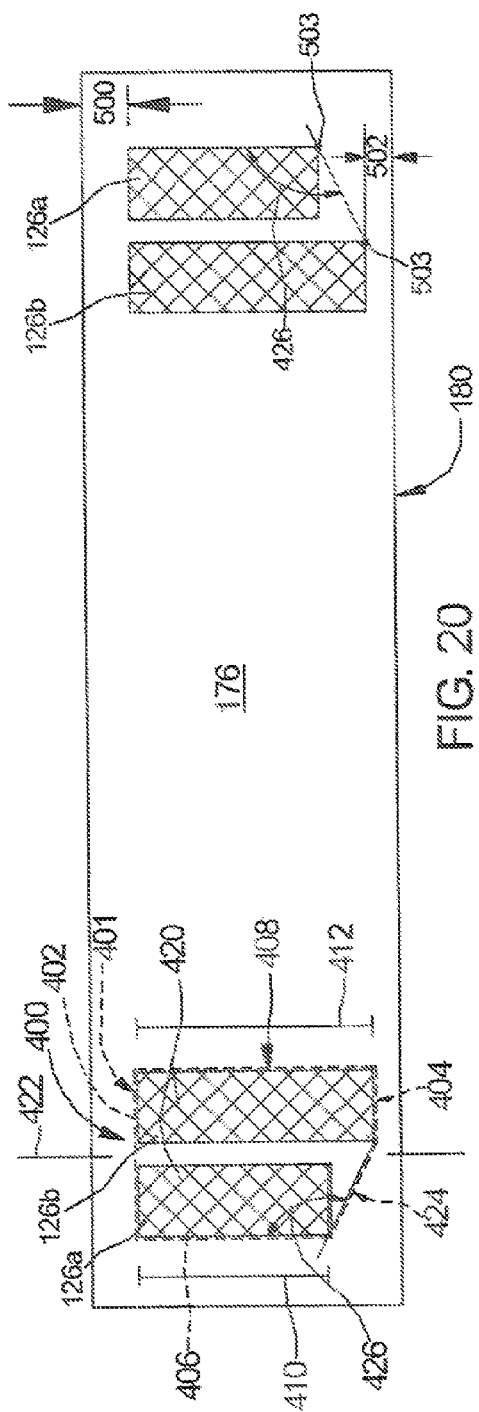
FIG. 20 is a top plan view of the secondary first fastener shown in FIGS. 6-8.

Referring now to FIG. 20, shown is an enlargement of the secondary first fastening components 126a and 126b (collectively referred to as fastening components 126). In this particular embodiment, the fastening components 126 can be generally described as a pair of rectangular islands 420 that occupy a region 400 which may be located on strip 180, as shown. Specifically, the region 400 is defined by an outline 401 having a straight waist edge 402 and an opposite leg edge 404, which are connected together by a straight outer edge 406 and connecting edge 424, and a straight inner edge 408. Therefore, the outline 401 is a figure having five sides that may be described as a rectangle with a truncated corner.

The length 410 of the outline's outer edge 406 is shorter than the length 412 of the outline's inner edge 408. This length difference provides at least one advantage to the wearer over that presented by the prior art fastening component 26, that is, there is less opportunity for the fastening component 126 to irritate and/or cause red-marking to the wearer's skin.

It should be observed that when the waist edge 402 is bisected by a normal axis-line 422, the area of fastening component 126a between the outer edge 406 and the axis line 422 is less than the area of fastening component 126b between the inner edge 408 and axis line 422.

It should further be observed that there is an obtuse angle 426 formed by the outer edge 406 and a straight line that connects each outer corner 503 near the leg edge of the islands 420. This line defines connecting edge 424. The obtuse angle 426 between connecting edge 424 and outer edge 406 may be between about 100 degrees and 150 degrees, or in other embodiments, between 110 and 140 degrees, and in yet other embodiments, between 115 and 130 degrees.

It is noted that the fastening component 126a and 126b need not be limited to rectangular shapes with normal corners, but instead, one or more of the corners could be defined by a radius (not shown). This may be done to make the fastening component 126 feel softer against the wearer's skin.

In the secondary fasting component embodiments shown in FIGS. 9-11 and 21, the islands 420 have a stacked configuration with respect to the waist edge 402.

Figure 21:
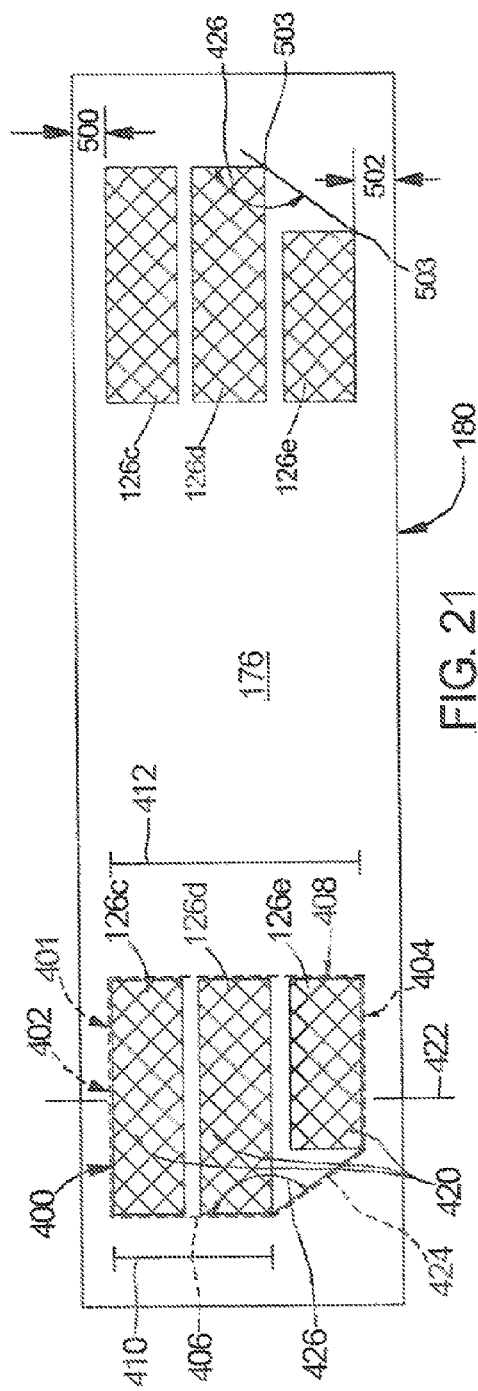
FIG. 21 is a top plan view of the secondary first fastener shown in FIGS. 9-11.

Referring now to FIG. 21, shown is an enlargement of the secondary first fastening components 126c-126e (collectively referred to as fastening components 126). In this particular embodiment, the fastening components 126 can be generally described as a trio of rectangular islands 420 that occupy a region 400 which may be located on strip 180, as shown. Specifically, the region 400 is defined by an outline 401 having a straight waist edge 402 and an opposite leg edge 404, which are connected together by a straight outer edge 406 and connecting edge 424, and a straight inner edge 408. Therefore, the outline 401 is a figure having five sides that may be described as a rectangle with a truncated corner.

The length 410 of the outline's outer edge 406 is shorter than the length 412 of the outline's inner edge 408. As with the other embodiments, this length difference provides at least one advantage to the wearer over that presented by the prior art fastening component 26 of FIG. 18, that is, there is less opportunity for the fastening component 126 to irritate and/or cause red-marking to the wearer's skin. In addition, the fastening component 126 requires less material than the prior-art fastening component 26.

It should be observed that when the waist edge 402 is bisected by a normal axis-line 422, the summation of the areas of fastening components 126c-126e located between the outer edge 406 and the axis line 422 is less than the summation of the areas of fastening components 126c-126e located between the inner edge 408 and axis line 422.

It is also noted that the area of each island represented by fastening components 126c and 126d is larger than the area of fastening component 126e.

It should further be observed that there is an obtuse angle 426 formed by the outer edge 406 and a straight line that connects each outer corner 503 near the leg edge of the islands 420. This line is the connecting edge 424. The obtuse angle 426 between connecting edge 424 and outer edge 406 may be between about 100 degrees and 150 degrees, or in other embodiments, between 110 and 140 degrees, and in yet other embodiments, between 115 and 130 degrees.

It is noted that the fastening components 126c-126e need not be limited to rectangular shapes with normal corners, but instead, one or more of the corners could be defined by a radius (not shown). This may be done to make the fastener feel softer against the skin.

In the secondary fasting component embodiment shown in FIGS. 12-14 and 22, the islands 420, a combination of secondary fastening components 126a, 126b, have a checkered configuration with respect to the waist edge 402.

Referring now to FIG. 22, shown is an enlargement of the secondary first fastening components 126f-126j (collectively referred to as fastening components 126). In this particular embodiment, the fastening components 126 can be generally described as a plurality of circular islands 420 that occupy a region 400 that may be located on strip 180 as shown. Specifically, the region 400 is defined by an outline 401 having a waist edge 402 and an opposite leg edge 404, which are connected together by an outer edge 406 and a straight connecting edge 424, and an inner edge 408. Therefore, the outline 401 is a figure having five sides that may be roughly described as a rectangle with a truncated corner.

The length 410 of the outline's outer edge 406 is shorter than the length 412 of the outline's inner edge 408. As with the other embodiments, this length difference provides at least one advantage to the wearer over that presented by the prior art fastening component 26 of FIG. 18, that is, there is less opportunity for the fastening component 126 to irritate and/or cause red-marking to the wearer's skin. In addition, the fastening component 126 requires less material than the prior-art fastening component 26 and the fastening components 126 shown in FIGS. 20 and 21. In addition, this configuration of islands 420 has no sharp edges, which may feel softer against the wearer's skin.

It should be observed that when the waist edge 402 is bisected by a normal axis-line 422, the summation of the areas of fastening components 126f and 126j, located between the outer edge 406 and the axis line 422, is less than the summation of the areas of fastening components 126g-126i, located between the inner edge 408 and axis line 422.

It should further be observed that there is an obtuse angle 426 formed by the straight portion of outer edge 406 and a straight line that connects tangents 505 near the leg edge of the islands 420. This line is the connecting edge 424. The obtuse angle 426 between connecting edge 424 and outer edge 406 may be between about 100 degrees and 150 degrees, or in other embodiments, between 110 and 140 degrees, and in yet other embodiments, between 115 and 130 degrees.

In the secondary fasting component embodiment shown in FIGS. 15-17 and 23, the islands 420, a combination of secondary fastening components 126a, 126b, have stacked configuration with respect to the waist edge 402.

Referring now to FIG. 23, shown is an enlargement of the secondary first fastening components 126k and 126l (collectively referred to as fastening components 126). In this particular embodiment, the fastening components 126 can be generally described as a pair of islands 420 that occupy a region 400 that may be located on strip 180 as shown. Specifically, the region 400 is defined by an outline 401 having a straight waist edge 402 and an opposite connecting edge 424 (coinciding with the leg edge 404), which are connected together by a straight outer edge 406 and a straight inner edge 408. Therefore, the outline 401 is a figure having five sides that may be described as a rectangle with a truncated corner.

The length 410 of the outline's outer edge 406 is shorter than the length 412 of the outline's inner edge 408. As with the other embodiments, this length difference provides at least one advantage to the wearer over that presented by the prior art fastening component 26 of FIG. 18, that is, there is less opportunity for the fastening component 126 to irritate and/or cause red-marking to the wearer's skin. In addition, the fastening component 126 requires less material than the prior-art fastening component 26.

It should be observed that when the waist edge 402 is bisected by a normal axis-line 422, the summation of the areas of fastening components 126k and 126l located between the outer edge 406 and the axis line 422 is less than the summation of the areas of fastening components 126k and 126l located between the inner edge 408 and axis line 422.

It is also noted that the area of the island 420 represented by fastening component 126k is larger than the area of the island 420 represented by fastening component 126l.

It should further be observed that there is an obtuse angle 426 formed by the outer edge 406 and the connecting edge 424. The obtuse angle 426 may be between about 100 degrees and 150 degrees, or in other embodiments, between 110 and 140 degrees, and in yet other embodiments, between 115 and 130 degrees.

In this embodiment, it should be noted that the fastening component 126l has a triangular shape. The triangle's outermost angle, located against the outer edge 406, is an acute angle. This outermost angle 428 may be between about 15 degrees and about 60 degrees, or in other embodiments the outermost angle of the second area is between about 20 degrees and about 45 degrees.

In some embodiments, an appearance of the secondary first fastening component 126, the secondary second fastening component 178, and/or the back ears may be configured to provide suitable visual cues to a user for attaching the diaper 110 to a wearer. For example, in some embodiments, a coloring of the secondary first fastening components 126 may be such so as to, e.g., increase the noticeability of the secondary first fastening components on the front portion 116 of the diaper 110. For example, each of the secondary first fastening components 126 may be configured as a different color than its immediate surroundings such that it stands out from its immediate surroundings. Similarly, a graphic, background pattern, etc., may be removed from the area surrounding the secondary first fastening components 126 to increase the noticeability of each component. Still further, an area on the front portion 116 of the diaper 110 where a corresponding secondary first fastening component 126 attaches may be provided with a different graphic or coloring, etc., than its surrounding, and the secondary first fastening components can correspondingly be constructed of a transparent or semi-transparent material such that, when the secondary first fastening component is provided on the front portion by any suitable means discussed herein, the different coloring, graphical properties, etc., are visible through the secondary first fastening component thus increasing the noticeability of the secondary first fastening components on the front portion.

In still further embodiments, the opacity of the pair of back ears 122 and/or the secondary second fastening component 178 may be configured such that each secondary first fastening component 126 is visible through a respective one of the ears 122 when the diaper 110 is in the wear configuration. For example, in some embodiments the back ears 122 and/or the secondary second fastening components 178 may be transparent or semi-transparent. In such embodiments, the secondary first fastening components 126 may be visible through the back ears 122 when the diaper is in the wear configuration so that a user may be provided with a visual indication of the engagement of each secondary first fastening component with the respective secondary second fastening component 178. In some embodiments, these visual cues (i.e., the coloring or graphical properties of the secondary first fastening component 126 and/or the opacity of the secondary second fastening component 178) may assist a user engaging the secondary fastening system and/or in ensuring the secondary fastening system is properly engaged in the wear configuration.

Figure 24:
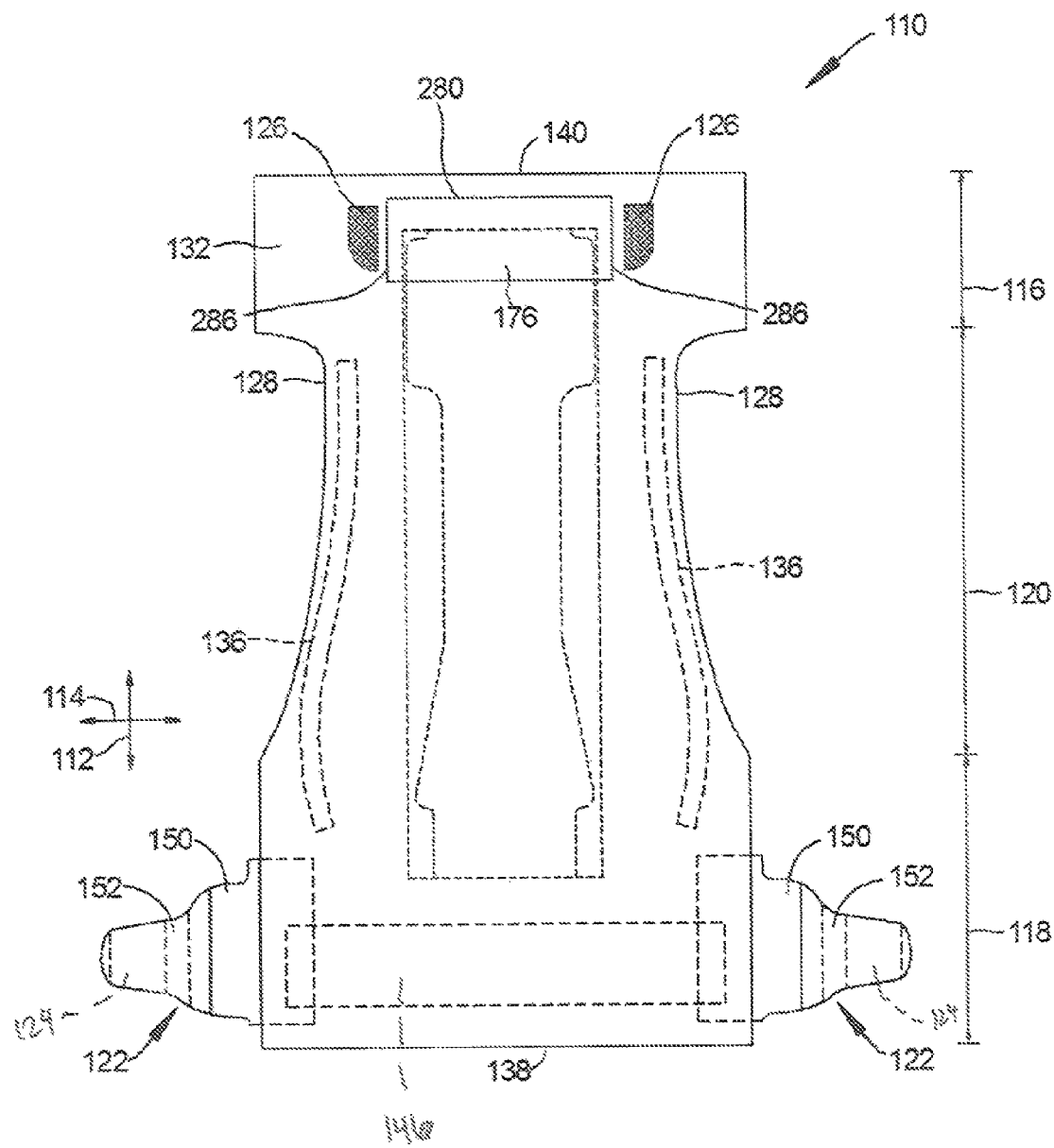
FIG. 24 is a is a top plan view of a diaper according to another embodiment in an unfolded and laid flat condition to show an outer surface of the diaper which faces away from the wearer when the diaper is worn, wherein the secondary first fastener is located on a strip.

Turning now to FIG. 24, another suitable embodiment of the diaper 110 according to some aspects of the disclosure is illustrated. Specifically, FIG. 24 depicts the diaper 110 in an unfolded and laid flat condition to again show the outer surface of the diaper which faces away from the wearer when the diaper is worn. In the depicted embodiment, the majority of the operable aspects of the diaper 110 are the same or substantially similar to the embodiment depicted in FIGS. 3-5 and as described herein. However, rather than providing secondary first fastening components 126 on the strip 180 as described, in the embodiment depicted in FIG. 24 the pair of secondary first fastening components are disposed directly on the outer cover 132.

Figure 6:
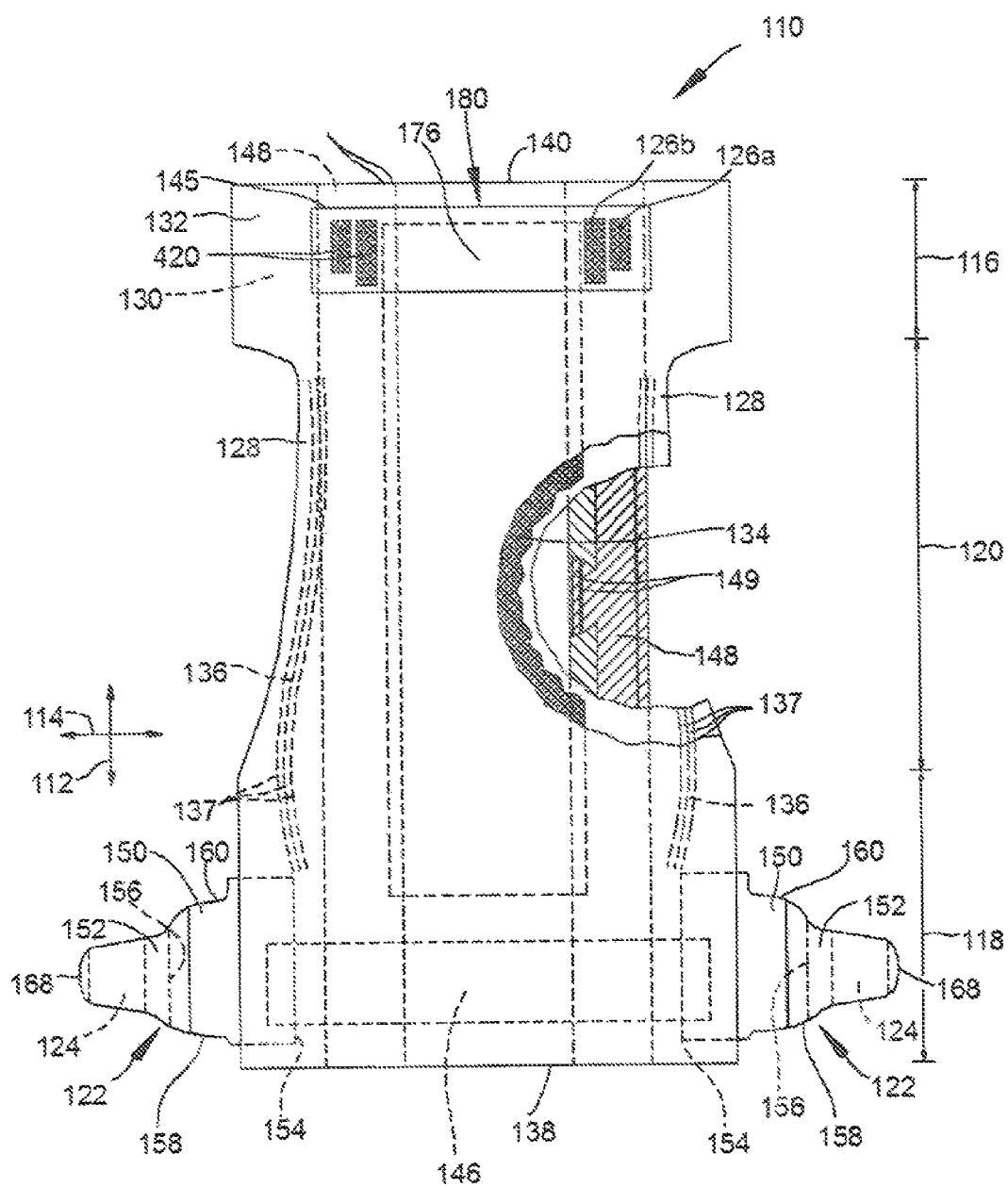
FIG. 6 is a top plan view of a diaper according to another embodiment in an unfolded and laid flat condition to show an outer surface of the diaper which faces away from the wearer when the diaper is worn.
Figure 7:
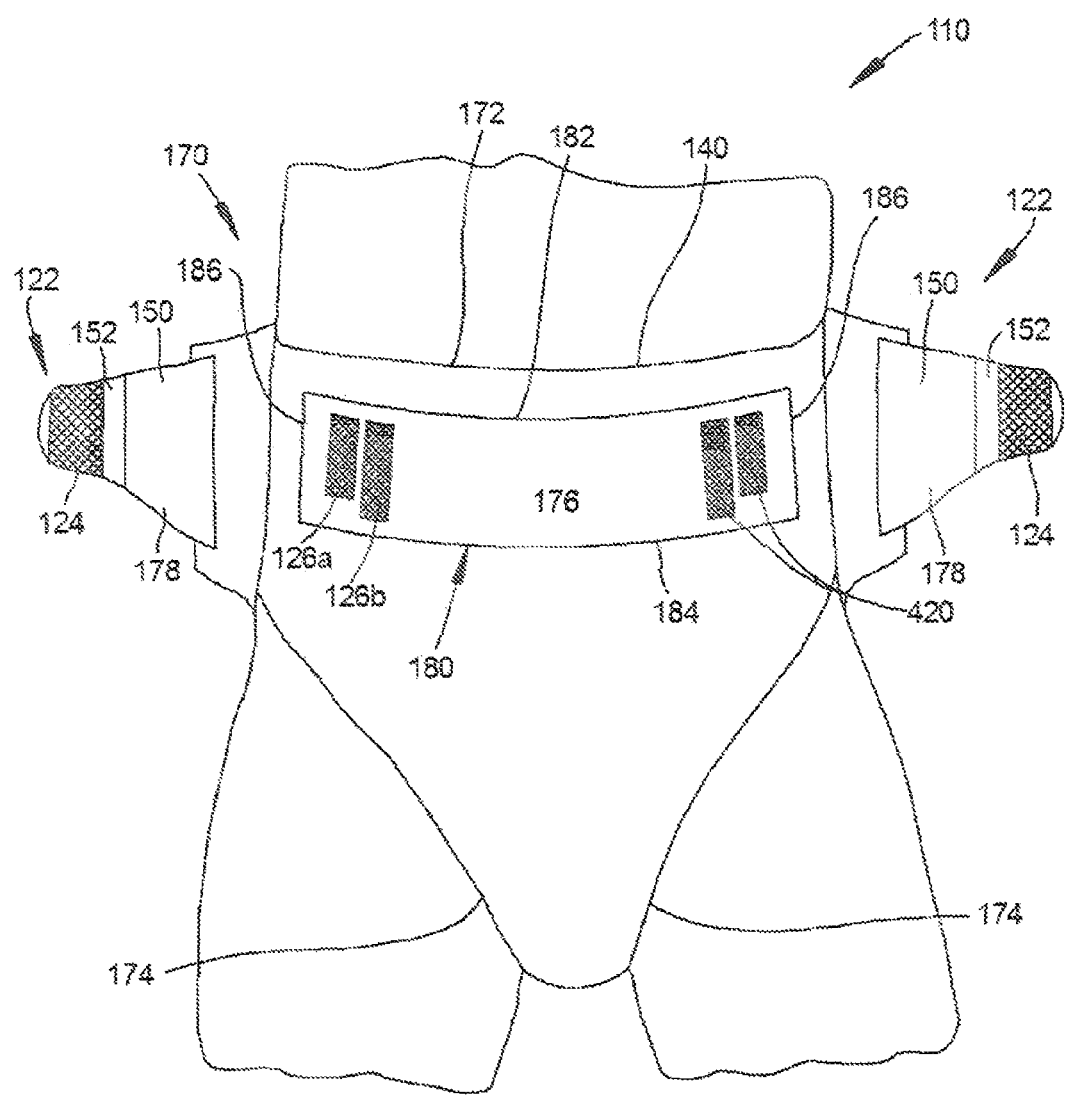
FIG. 7 is a front view of the diaper of FIG. 6 in a wear configuration, with the fastening system not fastened.
Figure 8:
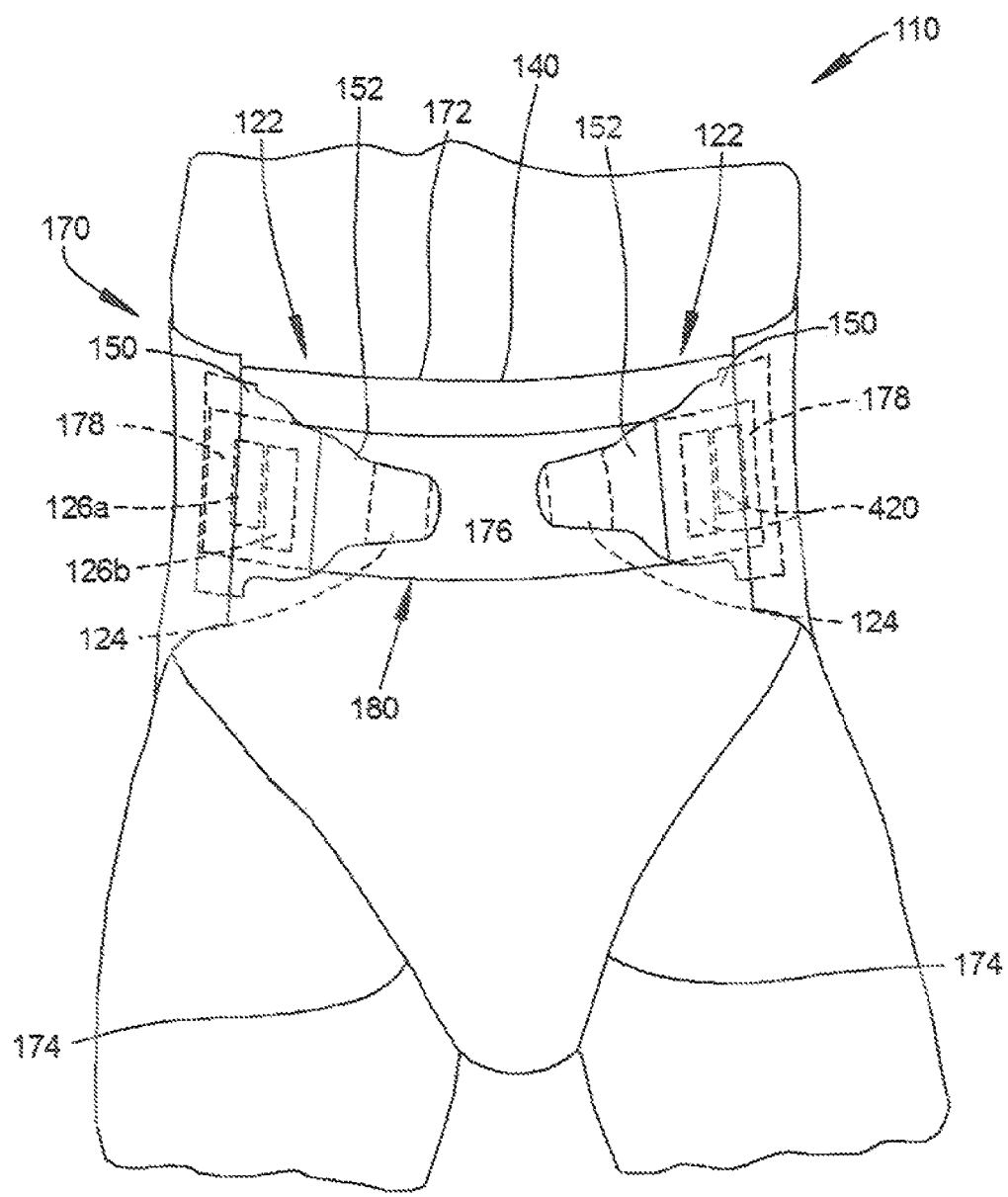
FIG. 8 is a front view of the diaper of FIG. 6 in a wear configuration, with the fastening system fastened.
Figure 9:
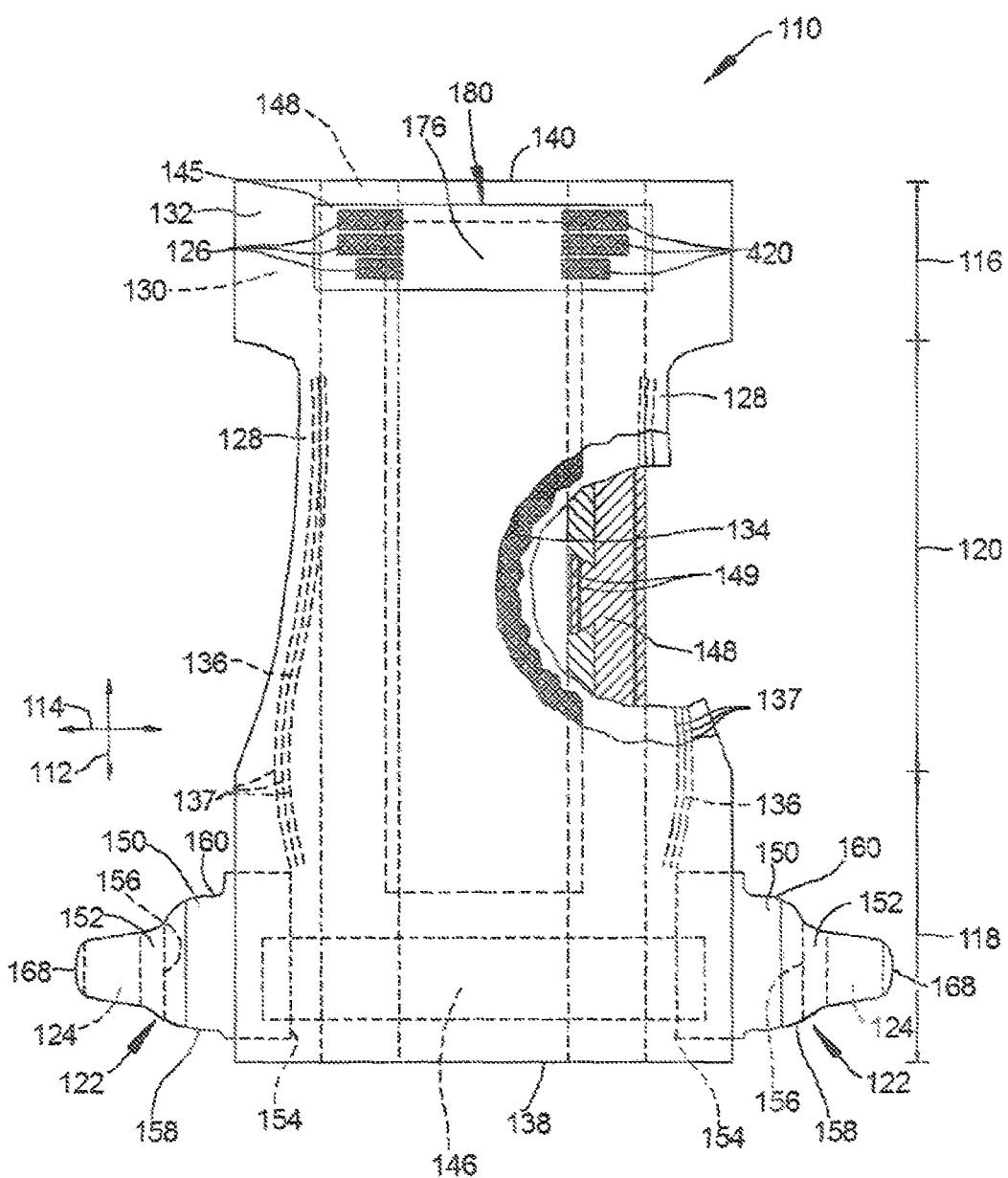
FIG. 9 is a top plan view of a diaper according to another embodiment in an unfolded and laid flat condition to show an outer surface of the diaper which faces away from the wearer when the diaper is worn.
Figure 10:
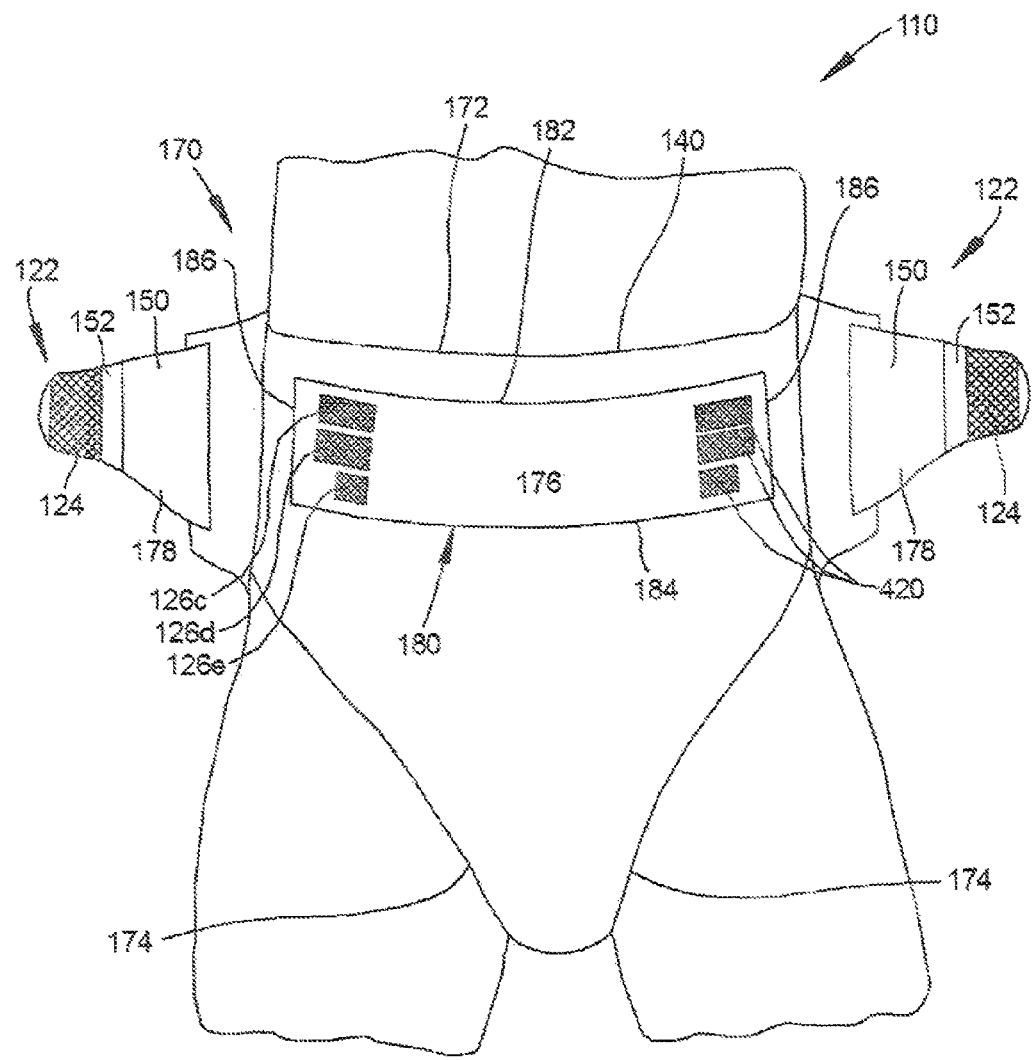
FIG. 10 is a front view of the diaper of FIG. 9 in a wear configuration, with the fastening system not fastened.
Figure 11:
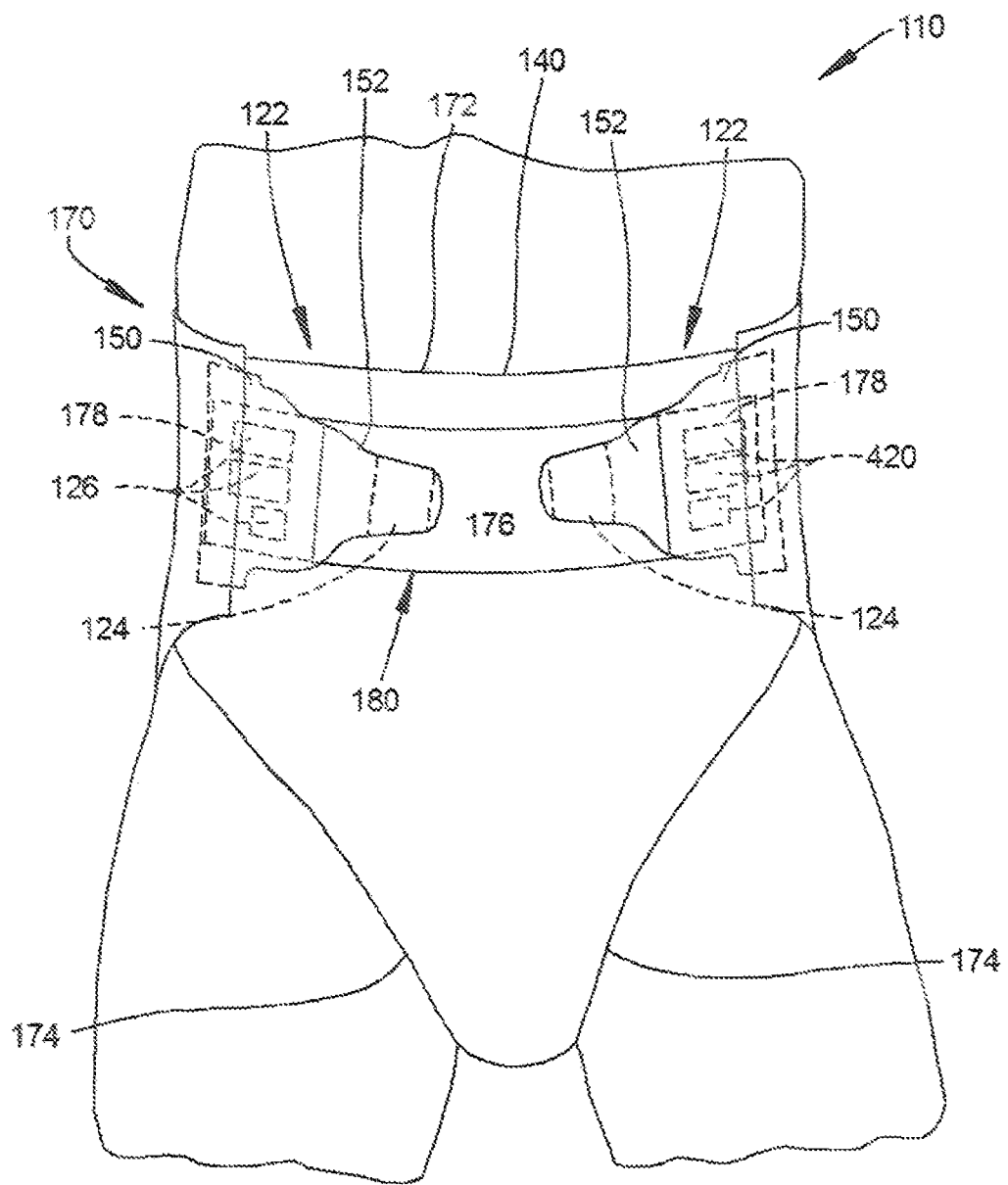
FIG. 11 is a front view of the diaper of FIG. 9 in a wear configuration, with the fastening system fastened.
Figure 12:
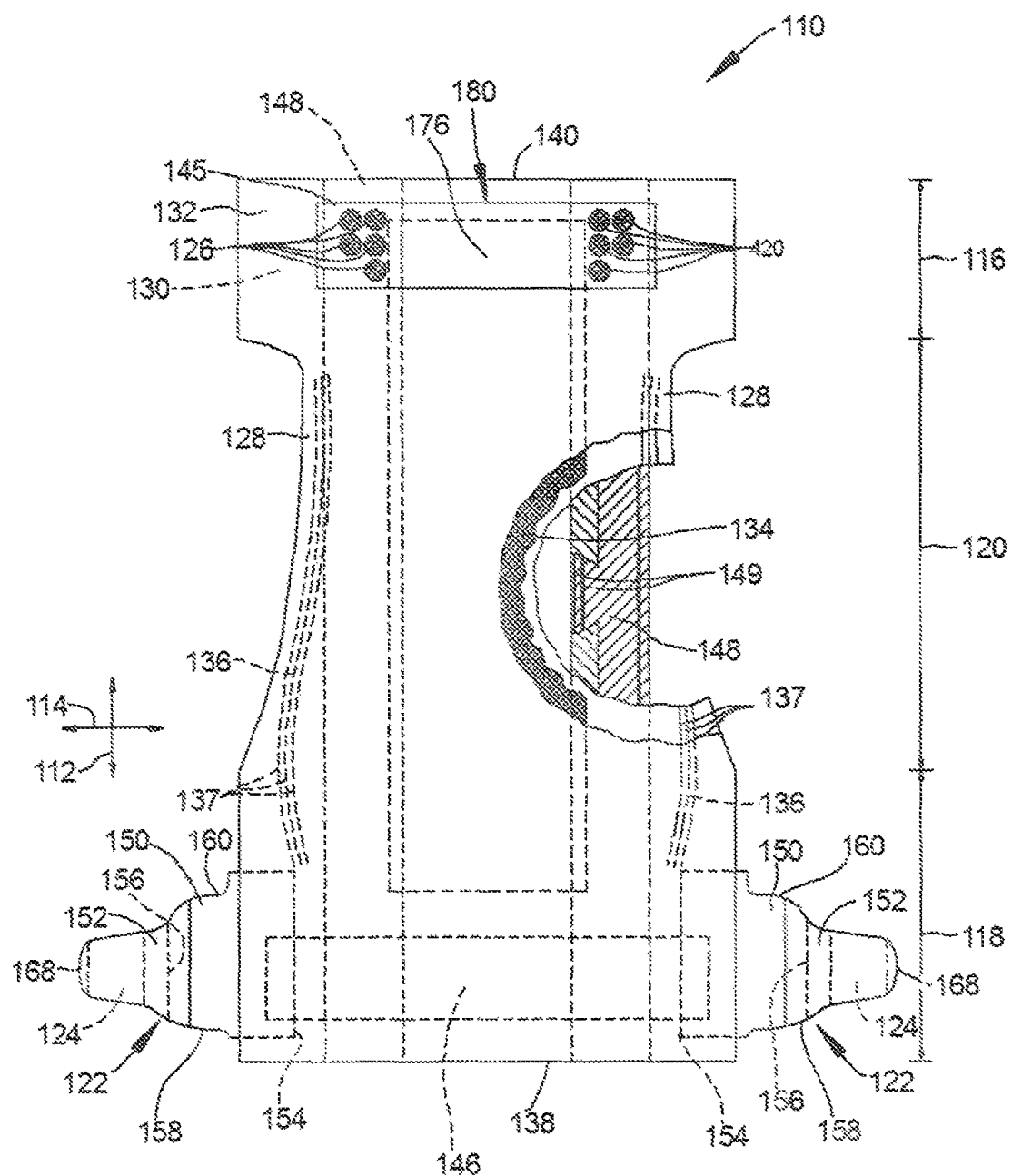
FIG. 12 is a top plan view of a diaper according to another embodiment in an unfolded and laid flat condition to show an outer surface of the diaper which faces away from the wearer when the diaper is worn.
Figure 13:
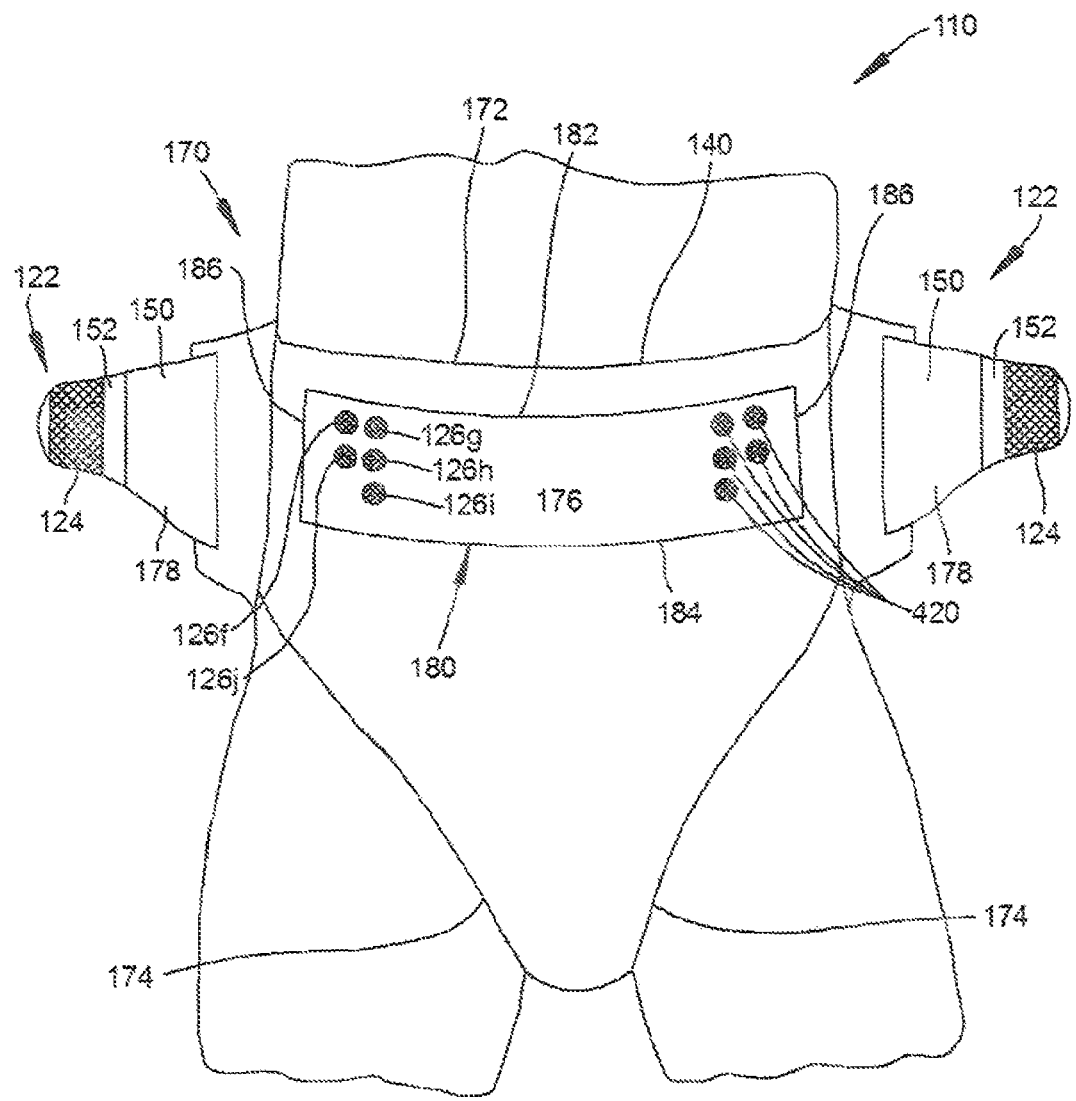
FIG. 13 is a front view of the diaper of FIG. 12 in a wear configuration, with the fastening system not fastened.
Figure 14:
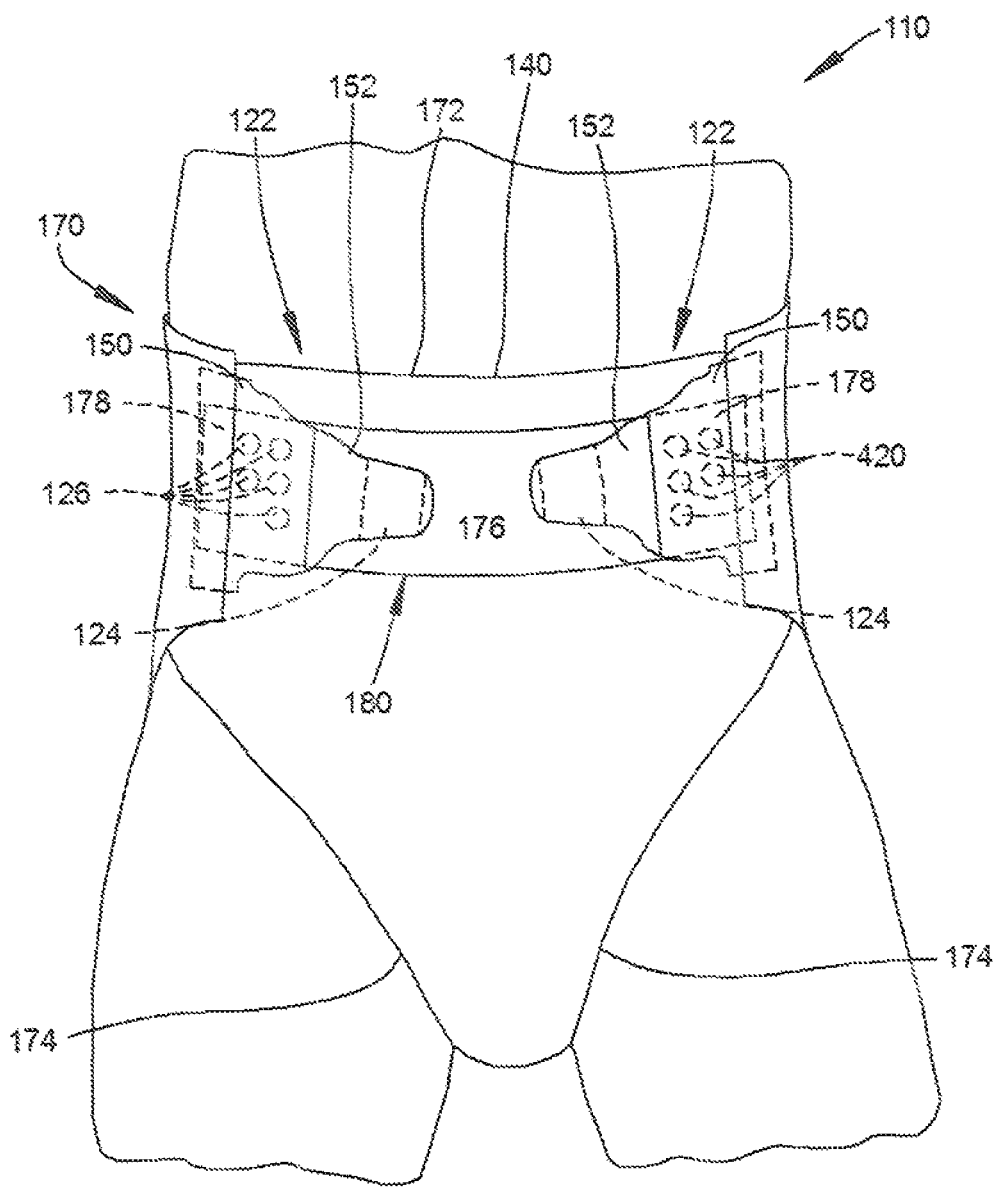
FIG. 14 is a front view of the diaper of FIG. 12 in a wear configuration, with the fastening system fastened.
Figure 15:
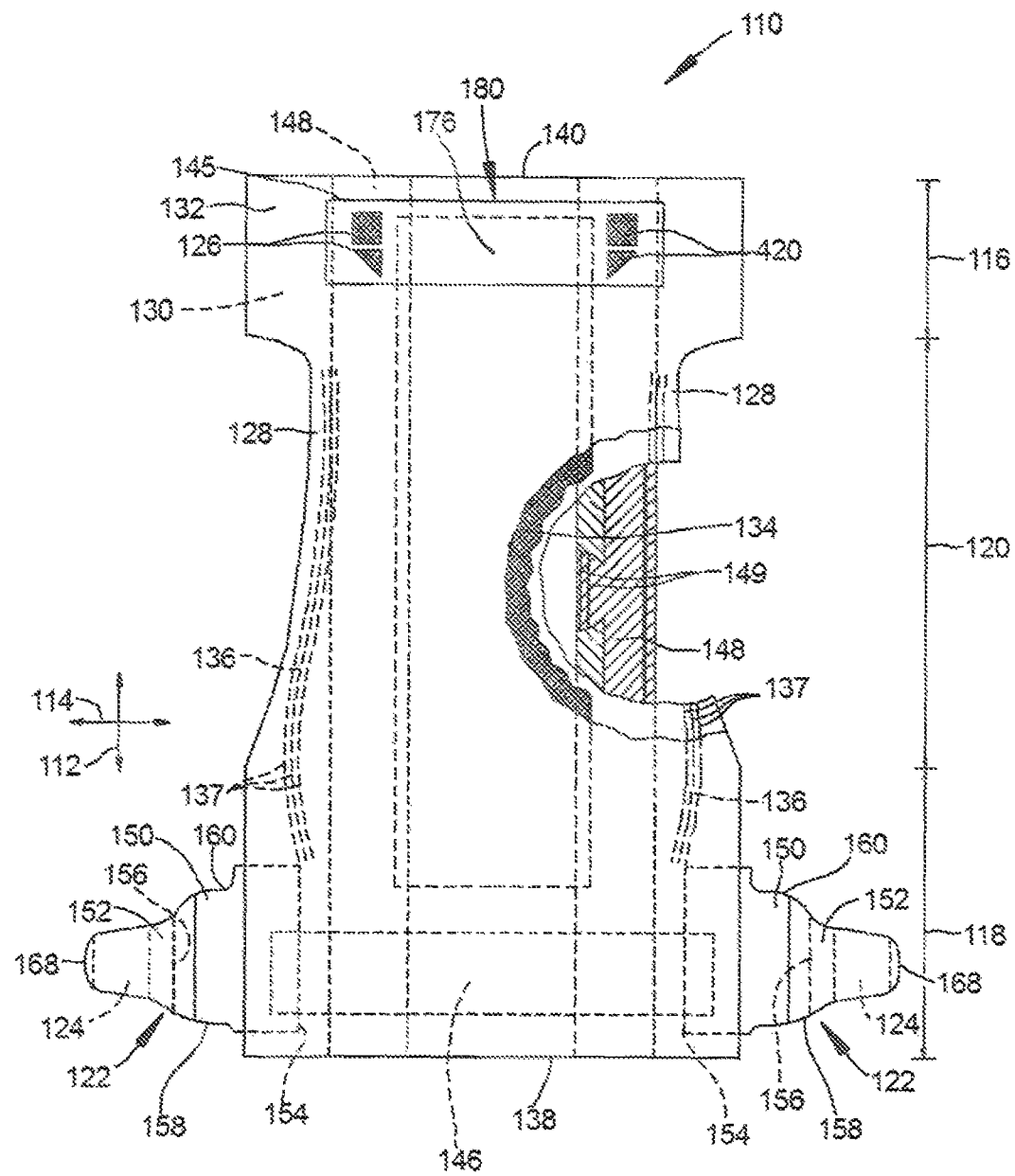
FIG. 15 is a top plan view of a diaper according to another embodiment in an unfolded and laid flat condition to show an outer surface of the diaper which faces away from the wearer when the diaper is worn.
Figure 16:
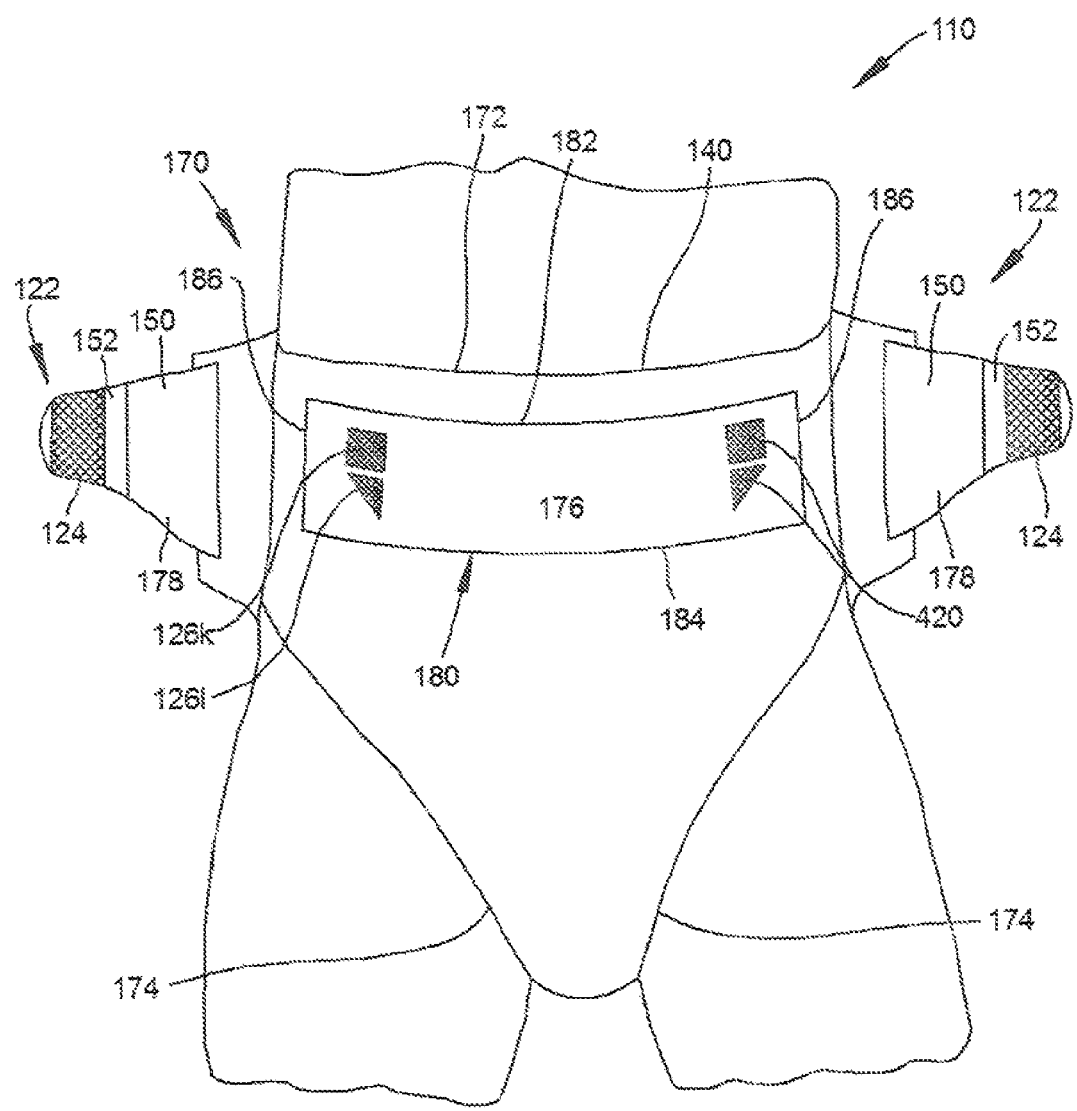
FIG. 16 is a front view of the diaper of FIG. 15 in a wear configuration, with the fastening system not fastened.
Figure 17:
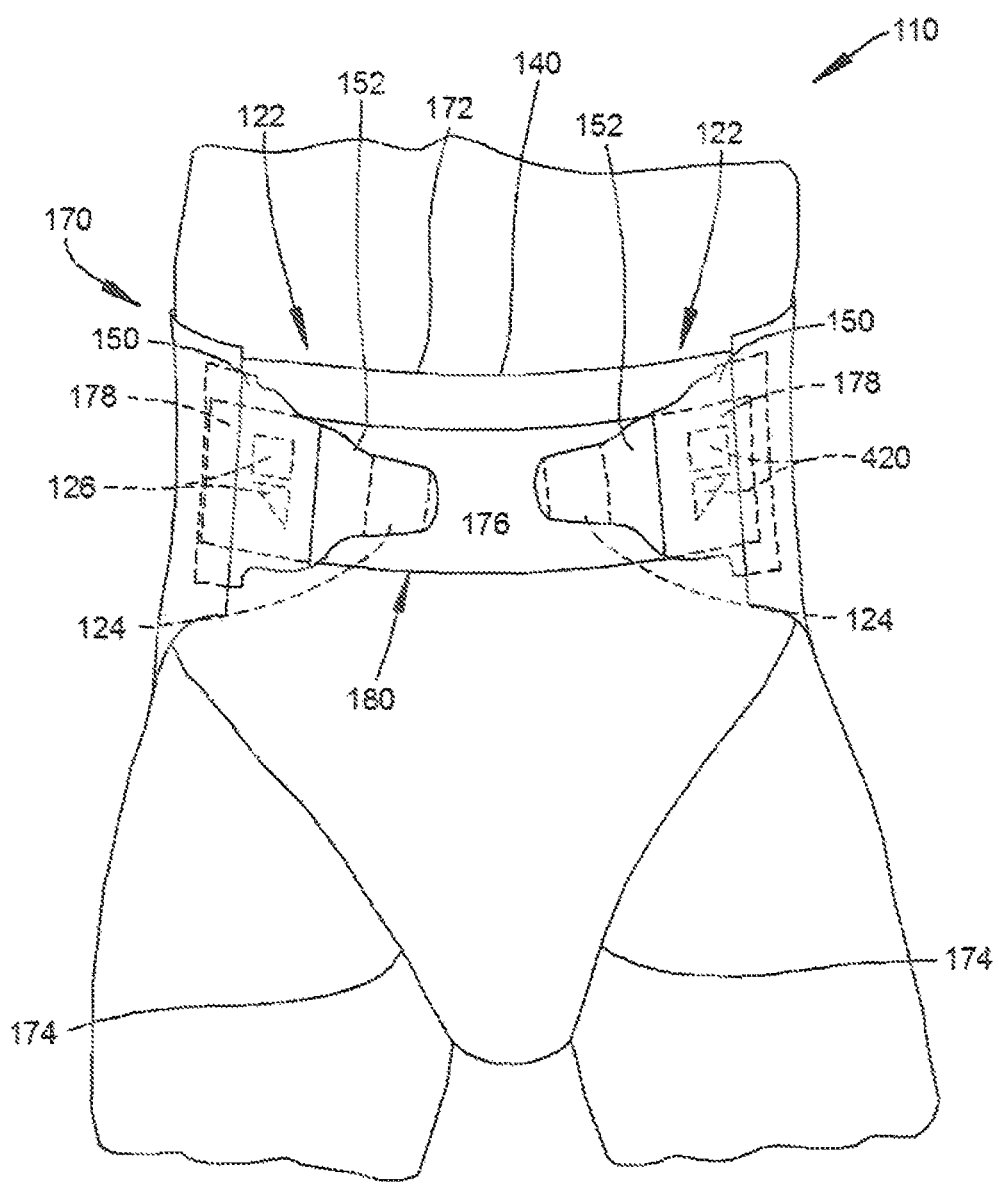
FIG. 17 is a front view of the diaper of FIG. 15 in a wear configuration, with the fastening system fastened.

More particularly, in the embodiment depicted in FIG. 6, the diaper 110 comprises a strip 280 which includes the primary secondary fastening component 176 and which is shorter in the lateral direction 114 than the strip 180. Unlike the strip 180, the strip 280 does not comprise the secondary first fastening components 126. Rather, the longitudinal edges 286 of the strip 280 are disposed inboard (i.e., closer to the center line 198 of the diaper 110) of the secondary first fastening components 126. Thus, and unlike the embodiment depicted in FIG. 3 where the secondary first fastening components 126 and the strip 180 may be formed as a single unit (e.g., a one piece extruded strip), in this embodiment the secondary first fastening components 126 will be formed separate from the strip 280 and attached directly to the outer cover 132 of the diaper 110.

Figure 25:
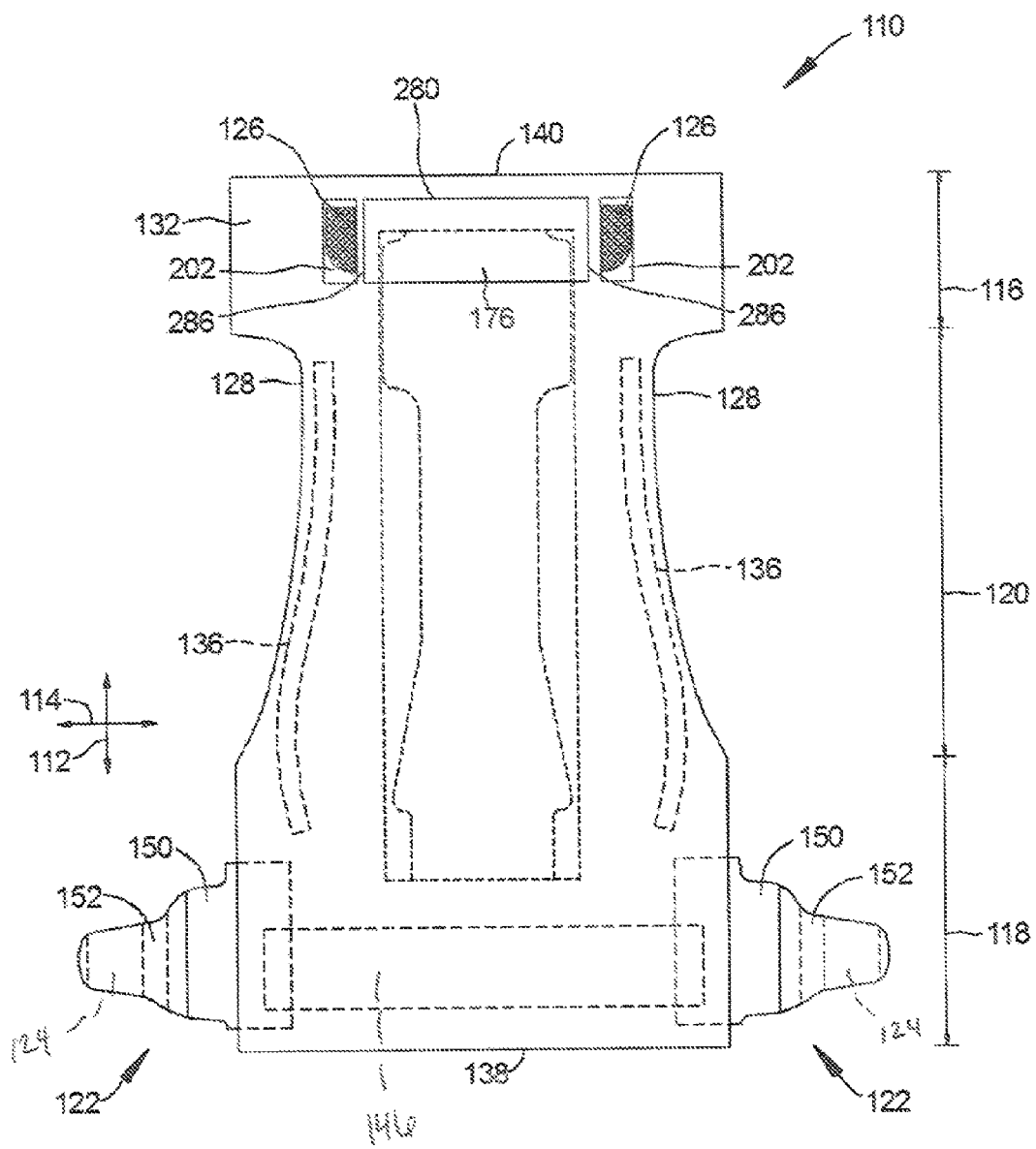
FIG. 25 is a top plan view of a diaper according to another embodiment in an unfolded and laid flat condition to show an outer surface of the diaper which faces away from the wearer when the diaper is worn, wherein the secondary first fastener is located on a strip.

FIG. 25 illustrates yet another suitable embodiment of the diaper 110 according to some aspects of the disclosure. Again, FIG. 25 depicts the diaper 110 in an unfolded and laid flat condition to show the outer surface of the diaper which faces away from the wearer when the diaper is worn. And again, the majority of the operable aspects of the diaper 110 are the same or substantially similar to the embodiments depicted in FIGS. 3-5 and FIG. 24.

However, in this embodiment, each of the secondary first fastening components 126 are provided on a corresponding carrier 202 which is then attached to or otherwise provided on the outer cover 132. As with the embodiment depicted in FIG. 6, in this embodiment the outer edges 286 of the strip 280 are disposed inboard of the secondary first fastening components 126. However, rather than attaching or otherwise providing the secondary first fastening components 126 directly to the outer cover 132, each secondary first fastening component is intermediately attached to a respective carrier 202 which is then embedded or otherwise attached to the outer cover using any of the discussed methods.

FIG. 26 illustrates yet another suitable embodiment of the diaper 110 according to some aspects of the disclosure. Once again, FIG. 26 depicts the diaper 110 in an unfolded and laid flat condition to show the outer surface of the diaper which faces away from the wearer when the diaper is worn. As with the embodiments depicted in FIG. 24 and FIG. 25, the majority of the operable aspects of the diaper 110 are the same or substantially similar to the embodiments depicted in the FIGS. 3-5.

However, in this embodiment, each of the secondary first fastening components 126 are provided on a corresponding carrier 302 which is then attached to or otherwise provided on the outer cover 132. Further, in this embodiment, outer edges 386 of a strip 380 (which includes primary second fastening component 176) overlap and attach to the carriers 302. That is, the innermost longitudinal edge 304 of each carrier 302 is disposed inboard of a corresponding outer edge 386 of the strip 380. In such embodiments, the carriers 302 may be embedded or otherwise provided to the outer cover 132 of the diaper with the strip 380 overlapping and attached to each of the carriers at a location near the outer edges 386 of the strip.

It is important to note that there may be manufacturing limitations affecting the placement of the secondary first fastening component on a patch 180 or other carrier, or on the diaper outer cover. Such limitations affect the shape of the fastening component. In particular, a triangle, square or rectangle may have rounded corners. Therefore, the terms "rectangle" and "triangle" are to be interpreted as shapes that may include those that have a radius at a corner instead of a sharp edge. It is also contemplated that the secondary first fastening components may include islands that are random in shape, or that are shaped into a recognizable figure such as a flower, a duck or any other imaginable figure.

As will be appreciated by those skilled in the art, changes and variations to the present disclosure are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the present disclosure. It is also to be understood that the scope of the present disclosure is not to be interpreted as limited to the specific aspects disclosed herein, but only in accordance with the appended claims when read in light of the foregoing disclosure.

What is claimed is:

1. An absorbent article comprising:
an absorbent assembly including longitudinally opposite ends, transversely opposite sides, a front waist region, a back waist region, and a crotch region extending longitudinally between and interconnecting the front and back waist regions, a liquid permeable inner layer for facing a wearer, an outer layer for facing away from the wearer, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly;
a pair of ears extending transversely outward from the opposite sides of the absorbent assembly in the back waist region, each of the ears comprising a primary first fastening-component that is selectively engagable with a primary second fastening-component in the front waist region of the absorbent assembly in a wear configuration of the article; and a pair of spaced-apart secondary first fastening-components disposed on the primary second fastening-component in the front waist region of the absorbent assembly, each of the secondary first fastening-components being selectively engageable with respective secondary second fastening-components in a wear configuration of the article;

wherein the secondary first fastening-components fit into respective fastener regions, each fastener region defined by an outline surrounding the secondary first-fastening components, wherein each outline has a waist edge and an opposite leg edge connected by an outer edge and an inner edge;

wherein the waist edge of each outline is spaced from a waist edge of the primary second fastening-component;

wherein the length of the outer edge is shorter than the length of the inner edge; and wherein the primary first fastening-components do not overlap the secondary first-fastening components in a wear configuration of the article.

2. The absorbent article of claim 1 wherein the secondary first-fastening components are discontinuous.

3. The absorbent article of claim 2 wherein the secondary-first fastening components comprise a plurality of islands, wherein each island has an area.

4. The absorbent article of claim 3 wherein the waist edge is bisected by a normal axis line, and the sum of the island areas between the outer edge and the axis line is less than the sum of the island areas between the inner edge and the axis line.

5. The absorbent article of claim 4 wherein the plurality of islands comprises two islands in a side-by-side configuration with respect to the waist edge.

6. The absorbent article of claim 4 wherein the plurality of islands comprises two islands in a stacked configuration with respect to the waist edge.

7. The absorbent article of claim 1 wherein there is an obtuse angle formed by the outer edge and the leg edge.

8. The absorbent article of claim 7 wherein the obtuse angle is between 100 degrees and 150 degrees.

9. An absorbent article comprising:

an absorbent assembly including longitudinally opposite ends, transversely opposite sides, a front waist region, a back waist region, and a crotch region extending longitudinally between and interconnecting the front and back waist regions, a liquid permeable inner layer for facing a wearer, an outer layer for facing away from the wearer, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly;

a pair of ears extending transversely outward from the opposite sides of the absorbent assembly in the back waist region, each of the ears comprising a primary first fastening-component that is selectively engagable with a primary second fastening-component in the front waist region of the absorbent assembly in a wear configuration of the article; and a pair of spaced-apart secondary first fastening-components disposed on the primary second fastening-component in the front waist region of the absorbent assembly, each of the secondary first fastening-components being selectively engageable with respective secondary second fastening-components in a wear configuration of the article;

wherein the secondary first fastening-components comprise continuous areas of secondary first fastening-material defining at least two discrete islands, a waist-region discrete island having a first area, and a leg-region discrete island having a second area, wherein the first area is larger than the second area;

wherein the primary first fastening-components do not overlap the secondary first-fastening components in a wear configuration of the article.

10. The absorbent article of claim 9 further comprising a middle discrete island having a third area located between the waist-region discrete island, and the leg-region discrete island, wherein the second area is smaller than the third area.

11. The absorbent article of claim 9 wherein the second area has a triangular shape.

12. The absorbent article of claim 11 wherein the outermost angle of the second area is an acute angle.

13. The absorbent article of claim 11 wherein the outermost angle of the second area is between 15 degrees and 60 degrees.

14. The absorbent article of claim 11 wherein the outermost angle of the second area is between 20 degrees and 45 degrees.

15. An absorbent article comprising:

an absorbent assembly including longitudinally opposite ends, transversely opposite sides, a front waist region, a back waist region, and a crotch region extending longitudinally between and interconnecting the front and back waist regions, a liquid permeable inner layer for facing a wearer, an outer layer for facing away from the wearer, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly;

a pair of ears extending transversely outward from the opposite sides of the absorbent assembly in the back waist region, each of the ears comprising a primary first fastening-component that is selectively engagable with a primary second fastening-component in the front waist region of the absorbent assembly in a wear configuration of the article; and a pair of spaced-apart secondary first fastening-components disposed on the primary second fastening-component in the front waist region of the absorbent assembly, each of the secondary first fastening-components being selectively engageable with respective secondary second fastening-components in a wear configuration of the article;

wherein the secondary first fastening-components are defined by rows of islands disposed within a rectangular region having a waist edge and an opposite leg edge connected by an outer edge and an inner edge, each island comprising a continuous area of secondary first fastening-material;

wherein each row of islands is comprised of one island and aligned with the inner edge;

wherein a row of islands adjacent the leg edge is shorter in a transverse direction than an adjacent row of islands; and wherein the primary first fastening-components do not overlap the secondary first-fastening components in a wear configuration of the article.

16. The absorbent article of claim 15 wherein there are two rows of islands, a first row of islands adjacent the waist edge, and a second row of islands adjacent the leg edge.

17. The absorbent article of claim 16 wherein the first row of islands consists of two islands, and the second row of islands consists of one island.

18. The absorbent article of claim 15 wherein each island of each row of islands has an area, and wherein the summation of areas in a row of islands adjacent the leg edge is less than the summation of areas in a row of islands immediately adjacent the thereto.

19. The absorbent article of claim 15 where there are three or more rows of islands.

20. The absorbent article of claim 15, wherein the waist edge of the rectangular region outline is spaced from a waist edge of the primary second fastening-component.

\* \* \* \* \*